United States Patent
Kuhn

(10) Patent No.: US 8,936,806 B2
(45) Date of Patent: Jan. 20, 2015

(54) PERIOSTIN INDUCES PROLIFERATION OF CARDIOMYOCYTES AND PROMOTES CARDIAC REGENERATION

(75) Inventor: Bernhard Kuhn, Brookline, MA (US)

(73) Assignee: Children's Medical Center Corporation, Boston, MA (US)

( * ) Notice: Subject to any disclaimer, the term of this patent is extended or adjusted under 35 U.S.C. 154(b) by 707 days.

(21) Appl. No.: 12/524,097

(22) PCT Filed: Jan. 22, 2008

(86) PCT No.: PCT/US2008/051659
§ 371 (c)(1),
(2), (4) Date: Feb. 11, 2010

(87) PCT Pub. No.: WO2008/091867
PCT Pub. Date: Jul. 31, 2008

(65) Prior Publication Data
US 2010/0166827 A1    Jul. 1, 2010

Related U.S. Application Data

(60) Provisional application No. 60/881,938, filed on Jan. 22, 2007.

(51) Int. Cl.
*A61F 2/00* (2006.01)
*C12N 5/077* (2010.01)
*A61K 38/17* (2006.01)

(52) U.S. Cl.
CPC .......... *C12N 5/0657* (2013.01); *A61K 38/1709* (2013.01); *C12N 2501/585* (2013.01); *C12N 2501/998* (2013.01)
USPC ............. 424/426; 424/93.7; 424/423; 514/12

(58) Field of Classification Search
None
See application file for complete search history.

(56) References Cited

U.S. PATENT DOCUMENTS

| 6,444,642 | B1 | 9/2002 | Sklar et al. |
| 2005/0042254 | A1* | 2/2005 | Freyman et al. ............. 424/426 |
| 2007/0264254 | A1 | 11/2007 | Zhou |

OTHER PUBLICATIONS

Gillan, L, D Matei, DA Fishman, CS Gerbin, BY Karlan, and DD Chang. 2002. Periostin secreted by epithelial ovarian carcinoma is a ligand for alpha v-beta 3 and alpha v-beta 5 integrins and promotes cell motility. Cancer Research; 62: 5358-5364.*
Visconti RP and RR Markwald. 2006. Recruitment of New Cells into the Postnatal Heart: Potential Modification of Phenotype by Periostin. Ann NY Acad Sci. 1080: 19-33.*
Nadal-Ginard B, J Kajstura, A Leri, and P Anversa. 2003. Myocyte Death, Growth, and Regeneration in Cardiac Hyperttrophy and Failure. Circ Res. 92: 139-150.*
Litvin J, S Zhu, R Norris, and R Markwald. 2006. Periostin Family of Proteins: Therapeutic Targets for Heart Disease. Anat Rec A Discov Mol Cell Evol Biol. 287(2): 1205-1212.*
Crackower, M.A. et al. Regulation of myocardial contractility and cell size by distinct PI3K-PTEN signaling pathways. Cell 110, 737-49 (2002).
del Monte, F. et al. Abrogation of ventricular arrhythmias in a model of ischemia and reperfusion by targeting myocardial calcium cycling. Proc Natl Acad Sci U S A 101, 5622-7 (2004).
Engel, F.B., et al. Proc. Natl. Acad. Sci. USA 103, 15546-15551 (2006).
Engel, F.B. et al. p38 MAP kinase inhibition enables proliferation of adult mammalian cardiomyocytes. Genes Dev 19, 1175-87 (2005).
Fazel, S. et al. Cardioprotective c-kit+ cells are from the bone marrow and regulate the myocardial balance of angiogenic cytokines. J Clin Invest 116, 1865-77 (2006).
He, T.C. et al. A simplified system for generating recombinant adenoviruses. Proc Natl Acad Sci U S A 95, 2509-14 (1998).
Howard, C.V. & Reed, M. Unbiased Stereology: Three-Dimensional Measurement in Microscopy, (BIOS Scientific Publishers, Oxford, 2005).
Hynes RO. Integrins: bidirectional, allosteric signaling machines. Cell 110:673-87. 2002.
Katsuragi, N. et al. Periostin as a novel factor responsible for ventricular dilation. Circulation 110, 1806-1813 (2004).
Litvin, J. et al. Cardiovasc. Pathol. 15, 24-32 (2006).
Ma, H., Sumbilla, C.M., Farrance, I.K., Klein, M.G. & Inesi, G. Am J Physiol Cell Physiol 286, C556-64 (2004).
Miranti, C.K. & Brugge, J.S. Sensing the environment: a historical perspective on integrin signal transduction. Nat Cell Biol 4, E83-90 (2002).
Nakajima, H., et al. Circ. Res. 94, 1606-1614 (2004); Woo, Y.J. et al. Circulation 114,1206-1213 (2006).
Pasumarthi, K.B., et al. Circ. Res. 96, 110-118 (2005).
Pasumarthi, K.B. & Field, L.J. Cardiomyocyte cell cycle regulation. Circ Res 90, 1044-54 (2002).
Prunier, F. et al. Am J Physiol Heart Circ Physiol (2006).
Rape, M. & Kirschner, M.W. Autonomous regulation of the anaphase-promoting complex couples mitosis to S-phase entry. Nature 432, 588-95 (2004).
Rubinson, D.A. et al. Nat. Genet. 33, 401-406 (2003).
Sadoshima, J. & Izumo, S. Annu Rev Physiol 59, 551-71 (1997).
Shi, Q. & King, R.W. Nature 437, 1038-42 (2005).
Soonpaa, M.H., Kim, K.K., Pajak, L., Franklin, M. & Field, L.J. Cardiomyocyte DNA synthesis and binucleation during murine development. Am J Physiol 271, H2183-9 (1996).
Strejan et al., J. Neuroimmunol. 7:27 (1984).

(Continued)

*Primary Examiner* — Carlos Azpuru
*Assistant Examiner* — David Browe
(74) *Attorney, Agent, or Firm* — Nixon Peabody LLP; David S. Resnick; Leena H. Karttunen Contarino

(57) ABSTRACT

The present invention provides compositions and methods for increasing proliferation, increasing cell cycle activity, and/or proliferation of postmitotic mammalian differentiated cardiomyocytes. The invention can be used to slow, reduce, or prevent the onset of cardiac damage caused by, for example, myocardial ischemia, hypoxia, stroke, or myocardial infarction in vivo. In addition, the methods and compositions of the invention can be used to enhance proliferation of differentiated cardiomyocytes in vitro and/or ex vivo, which can then be used in tissue grafting.

9 Claims, 17 Drawing Sheets

(56) References Cited

OTHER PUBLICATIONS

Tai, I.T., Dai, M. & Chen, L.B. Carcinogenesis 26, 908-15 (2005).
Litvin, J. et al., Cardiovascular Pathlogy, vol. 13, pp. S139-S200, XP02573717 abstract.
Litvin, J. et al., The Anatomical Record, Part A, Discoveries in Molecular, Cellular, and Evolutionary Biology, vol. 287, pp. 1205-1212, 2005.
Kim et al., International Journal of Cancer, vol. 117, pp. 51-58, 2005.
Ahuja et al., Cardiac myocyte cell cycle control in development, disease, and regeneration. Physiol Rev. Apr. 2007;87 (2):521-44.
Bersell et al., Neuregulin1/ErbB4 signaling induces cardiomyocyte proliferation and repair of heart injury. Cell. Jul. 23, 2009;138(2):257-70.
Bettencourt-Dias et al., Heterogeneous proliferative potential in regenerative adult newt cardiomyocytes. J Cell Sci. Oct. 1, 2003;116(Pt 19):4001-9. Epub Aug. 19, 2003.
Chaudhry et al., Cyclin A2 mediates cardiomyocyte mitosis in the postmitotic myocardium. J Biol Chem. Aug. 20, 2004;279(34):35858-66. Epub May 24, 2004.
Engel et al., FGF1/p38 MAP kinase inhibitor therapy induces cardiomyocyte mitosis, reduces scarring, and rescues function after myocardial infarction. Proc Natl Acad Sci U S A. Oct. 17, 2006;103(42):15546-51. Epub Oct. 10, 2006.
Fuller et al., ErbB receptors, their ligands, and the consequences of their activation and inhibition in the myocardium. J Mol Cell Cardiol. May 2008;44(5):831-54. Epub Mar. 4, 2008.
Gao et al., A Phase II, randomized, double-blind, multicenter, based on standard therapy, placebo-controlled study of the efficacy and safety of recombinant human in patients with chronic heart failure. J Am Coll Cardiol. May 4, 1010:55(18):1907-14.
Gassmann et al., Aberrant neural and cardiac development in mice lacking the ErbB4 neuregulin receptor. Nature. Nov. 23, 1995;378(6555):390-4.
Golub et al., Behavioral characteristics of a nervous system-specific erbB4 knock-out mouse. Behav Brain Res. Aug. 12, 2004;153(1):159-70.
Guha et al., Organ renewal and cell divisions by differentiated cells in Drosophila. Proc Natl Acad Sci U S A. Aug. 5, 2008;105(31):10832-6. Epub Jul. 29, 2008.
Hoover, John E., Remington's Pharmaceutical Sciences, (1975), Mack Publishing Co., Easton, Pennsylvania Table of Contents. 3 pages.

International Preliminary Report on Patentability mailed Feb. 2, 2012 for Application No. PCT/US2010/042565 (7 pages).
International Search Report and Written Opinion mailed Apr. 20, 2011 for Application No. PCT/US2010/042565 (13 pages).
Jackson-Fisher et al., Formation of Neu/ErbB2-induced mammary tumors is unaffected by loss of ErbB4. Oncogene. Sep. 14, 2006;25(41):5664-72. Epub May 1, 2006.
Keefe DL. Trastuzumab-associated cardiotoxicity. Cancer. Oct. 1, 2002;95(7):1592-600.
Kühn et al., Periostin induces proliferation of differentiated cardiomyocytes and promotes cardiac repair. Nat Med. Aug. 2007;13(8):962-9. Epub Jul. 15, 2007.
Lee et al., Requirement for neuregulin receptor erbB2 in neural and cardiac development. Nature. Nov. 23, 1995;378 (6555):394-8.
Lieberman et al., (1980) Eds., Pharmaceutical Dosage Forms, Marcel Decker, New York, N.Y Table of Contents. 21 pages.
Liu et al., Neuregulin-1/erbB-activation improves cardiac function and survival in models of ischemic, dilated, and viral cardiomyopathy. J Am Coll Cardiol. Oct. 3, 2006;48(7):1438-47. Epub Sep. 14, 2006.
Meyer et al.,Multiple essential functions of neuregulin in development. Nature. Nov. 23, 1995;378(6555):386-90. Erratum in: Nature Dec. 14, 1995;378(6558):753.
Sawyer, Peptide Based Drug Design, ACS, Washington (1995) Table of Contents. 38 pages.
Soriano, Generalized lacZ expression with the ROSA26 Cre reporter strain. Nat Genet. Jan. 1999;21(1):70-1.
Weaver et al., Dual origin of tissue-specific progenitor cells in Drosophila tracheal remodeling. Science. Sep. 12, 2008;321(5895):1496-9. Epub Jul. 31, 2008.
Wills et al., Regulated addition of new myocardial and epicardial cells fosters homeostatic cardiac growth and maintenance in adult zebrafish. Development. Jan. 2008;135(1):183-92. Epub Nov. 28, 2007.
Yoshizumi et al., Disappearance of cyclin A correlates with permanent withdrawal of cardiomyocytes from the cell cycle in human and rat hearts. J Clin Invest. May 1995;95(5):2275-80.
Zhao et al., Neuregulins promote survival and growth of cardiac myocytes. Persistence of ErbB2 and ErbB4 expression in neonatal and adult ventricular myocytes. J Biol Chem. Apr. 24, 1998;273(17):10261-9.

\* cited by examiner

A.

B.

PERIOSTIN INDUCES PROLIFERATION OF CARDIOMYOCYTES AND PROMOTES CARDIAC REGENERATION

RELATED APPLICATIONS

This application claims priority of U.S. Provisional Application No. 60/881,938 filed Jan. 22, 2007, which is incorporated by reference in its entirety.

GOVERNMENT SUPPORT

This invention was made with government support under Grant No. AHA 0425772T awarded by the American Heart Association. The U.S. government has certain rights in this invention.

BACKGROUND OF THE INVENTION

Cardiovascular diseases are a leading cause of death resulting in almost 40% of deaths annually in the United States. Inadequate human myocardial regeneration poses a significant public health problem. It is estimated that 13 million Americans have coronary artery disease, and more than half a million experience a myocardial infarction every year. Human cardiac tissue responds to injury, e.g. myocardial infarction, with scar formation. Because the human heart is incapable of adequate muscle regeneration, survivors of a myocardial infarction typically develop heart failure, arrhythmias, thrombosis, and other complications.

Adult human hearts do not regenerate after injury; instead, the defect is replaced by fibrotic tissue. Most evidence to date indicates that cardiomyocyte proliferation, the cellular basis of regeneration, is not a significant component of the mammalian response to acute injury. In contrast to adult cardiomyocytes, fetal cardiomyocytes do proliferate during development.

Heart disease results in the loss of cardiomyocytes. It has been a significant challenge to develop effective treatments for cardiac repair because adult mammalian cardiomyocytes are highly differentiated cells and have been believed to be unable to proliferate. Mammalian cardiomyocytes withdraw from the cell cycle soon after birth and have lowered levels of cyclin A (Yoshizumi, M., et. al. (1995). *J Clin Invest* 95, 2275-2280). The fact that primary cardiac tumors occur rarely supports the notion that adult cardiomyocytes are highly restricted in their ability to divide. Because of its lack of proliferative potential, the primary response of the mammalian heart to injury is scar formation, which prevents cardiac repair. Thus the loss of cardiomyocytes after damage caused by events such as myocardial infarction generally results in compensatory responses that are inadequate to restore function. Unreplaced loss of cardiomyocytes leads to heart failure, a significant health problem worldwide.

Current therapies are also limited in their effectiveness. In order to sufficiently repair cardiac injury, it is necessary to provide a source of new cardiomyocytes. Proliferation of differentiated endogenous cardiomyocytes can enhance the regenerative capacity of mammalian hearts.

Accordingly, there is a need in the art for methods of increasing and/or promoting proliferation of adult mammalian cardiomyocytes.

SUMMARY OF THE INVENTION

The present invention provides compositions and methods for increasing proliferation, increasing cell cycle activity, and/or proliferation of postmitotic mammalian differentiated cardiomyocytes. The invention can be used to slow, reduce, or prevent the onset of cardiac damage caused by, for example, myocardial ischemia, hypoxia, stroke, or myocardial infarction in vivo. In addition, the methods and compositions of the invention can be used to enhance proliferation of differentiated cardiomyocytes in vitro and/or ex vivo, which can then be used in tissue grafting.

The invention is based, in part, on the discovery that periostin, a component of the extracellular matrix, and fragments thereof promote cardiomyocyte proliferation and myocardial regeneration. The adult mammalian heart responds to injury with scar formation, not with proliferation, the cellular basis for regeneration. The insufficient regeneration of mammalian hearts is explained by the contractile apparatus impinging on cardiomyocyte division. The invention demonstrates that extracellular periostin can induce cell cycle re-entry of differentiated mammalian cardiomyocytes. Periostin stimulates mononuclear cardiomyocytes, present in the adult mammalian heart, to undergo the full mitotic cell cycle. Periostin activates $\alpha V\beta 1/3/5$ integrins located in the cardiomyocyte cell membrane. Periostin-induced cardiomyocyte proliferation results from activation the ERK1/2 and Akt signaling pathways. After myocardial infarction, recombinant periostin induces cardiomyocyte cell cycle re-entry, improves cardiac remodeling and function, reduces fibrosis and infarct size, and increases angiogenesis. These results demonstrate that periostin and the pathway it regulates is a new target for innovative strategies to treat heart failure.

The invention identifies pathways that can induce proliferation of differentiated cardiomyocytes as a potential route to restore cardiac function. In another aspect of the invention, agents are disclosed that activate the signal transduction cascade consisting of extracellular periostin, integrins, and the ERK1/2 and the PI3-kinase/Akt pathways. Such agents include periostin, truncated biologically active constructs of periostin, functional analogs of periostin and pharmaceutically acceptable derivatives of periostin or its functional analogs, and combinations thereof.

In another aspect, the invention discloses methods of stimulating proliferation of post-mitotic cells using compounds comprising periostin, fragments or variants thereof, or pharmaceutically acceptable derivatives thereof. The post-mitotic cells can be cardiomyocytes, and preferably mammalian cardiomyocytes. In some embodiments, proliferation comprises at least one of cell cycle reentry, increased cardiomyocyte DNA synthesis and cytokinesis. In some embodiments, periostin, fragments or variants thereof, is delivered locally.

In another aspect, the invention discloses a method of inducing division of post mitotic cells, comprising administering an integrin activator or a pharmaceutically acceptable derivative thereof to a subject in an amount effective to stimulate de-differentiation of post-mitotic cells. The integrin activator activates at least one of the integrin subunits selected from the group comprising $\alpha V$, $\beta 1$, and $\beta 3$, and $\beta 5$ integrin subunits. The integrin activator can be periostin or fragments thereof. In some embodiments, activation of integrin causes ERK1/2 and/or Akt phosphorylation. In some embodiments, the integrin activator or a pharmaceutically acceptable derivative thereof can be delivered locally to the target cells or target area. Local and/or targeted delivery can be administered using a slow controlled release delivery system, such as, for example, a biodegradable matrix. The invention can be used with a long-term, short-term and/or controlled release delivery systems.

In another aspect, the invention provides a method of repairing heart tissue, comprising identifying a subject in need of heart tissue repair, and administering to the subject an effective amount of αVβ1/3/5 integrin activator, such that proliferation of cardiomyocytes increases. The integrin activator can be periostin or fragments thereof. In some embodiments, the subject in need of heart tissue repair has undergone myocardial ischemia, hypoxia, stroke, or myocardial infarction.

In another aspect, the invention provides a method for producing de-differentiated of cardiomyocytes comprising selecting differentiated cells from a tissue that includes said cells; resuspending said concentrated cells in a growth medium containing an effective amount of integrin activator; and culturing said resuspended cells in the growth medium for a time and under conditions to effect de-differentiation of at least a portion of said selected cells in culture, wherein at least a portion of said selected terminally differentiated cells in culture undergo at least one round of cardiomyocyte division. The integrin activator can be periostin or fragments thereof.

DETAILED DESCRIPTION OF THE INVENTION

Figure 1:
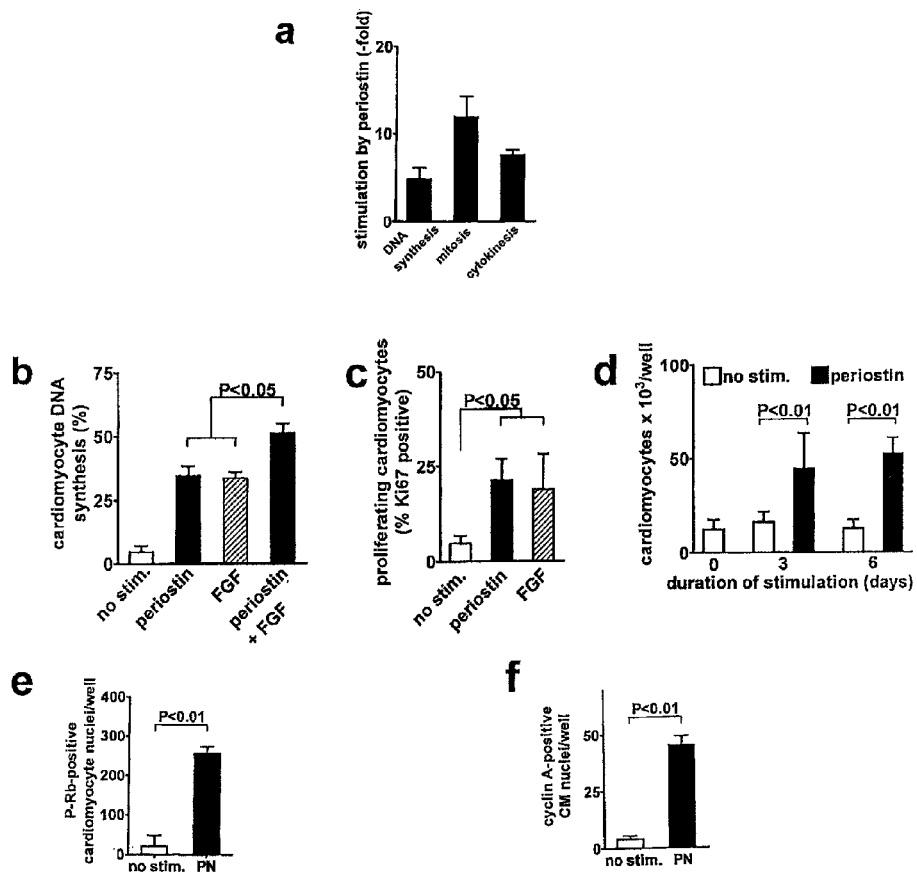
FIG. 1a is a bar graph showing that periostin stimulates DNA synthesis, mitosis, and cytokinesis in primary neonatal rat ventricular cardiomyocytes after stimulation with periostin for 3 days.
FIG. 1b is a bar graph demonstrating the additive effect of periostin and FGF on DNA synthesis.
FIG. 1c is a bar graph demonstrating the percent proliferating cardiomyocytes following stimulation with periostin and FGF determined by expression of marker Ki67.
FIG. 1d is a bar graph demonstrating cardiomyocyte proliferation 0, 3, and 6 days following stimulation with periostin and FGF determined by cell count.
FIG. 1e is a bar graph showing the amount of phosphorylated retinoblastoma protein (P–Rb) positive cardiomyocyte nuclei following stimulation with periostin and inactivation of cell cycle inhibitor retinoblastoma protein determined with antibody against phosphorylated retinoblastoma protein (P–Rb)
FIG. 1f is a bar graph demonstrating nuclear accumulation of cell cycle activator cyclin A.

So that the invention is more clearly understood, the following terms are defined:

The term "portion" or "fragment" as used herein refers to an amino acid sequence of the periostin genes that has fewer amino acids than the entire sequence of the periostin genes. For example, a periostin fragment can comprise one, two, three or four of the fasciclin 1 (fas1) domains. In some embodiments, the periostin fragment comprises the four fasciclin 1 (fas1) domains. In some embodiments, the periostin fragment that comprise a fas1 domain can include additional amino acids to facilitate the binding of the protein fragment. For example, a periostin fragment comprising fas1 can include 10%, 20%, 30%, 40%, or 50%, etc. of the amino acids comprising fas2.

"Variant" as the term is used herein, is a protein that differs from a reference protein (i.e. a periostin protein or fragment thereof consistent with embodiments of the present invention), but retains essential properties (i.e., biological activity). A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. Generally, differences are limited so that the sequences of the reference polypeptide and the variant are closely similar overall and, in many regions, identical.

A variant and reference protein may differ in amino acid sequence by one or more substitutions, additions, and deletions in any combination. A substituted or inserted amino acid residue may or may not be one encoded by the genetic code. A variant of a protein may be naturally occurring such as an allelic variant, or it may be a variant that is not known to occur naturally. Non-naturally occurring variants of polynucleotides and polypeptides may be made by mutagenesis techniques or by direct synthesis. For instance, a conservative amino acid substitution may be made with respect to the amino acid sequence encoding the polypeptide.

Variant proteins encompassed by the present application are biologically active, that is they continue to possess the desired biological activity of the native protein, as described herein. The term "variant" includes any polypeptide having an amino acid residue sequence substantially identical to a sequence specifically shown herein in which one or more residues have been conservatively substituted with a functionally similar residue, and which displays the ability to mimic the biological activity of periostin, such as for example, activating integrins, phosphorylating ERK1/2 and Akt, and/or increasing proliferation of cardiomyocytes. "Biological activity," as used herein refers to the ability of the protein to increase DNA synthesis in cardiomyocytes, as can be tested by methods known to one skilled in the art, such as, but not limited to, BrdU uptake assay. Variants may result from, for example, genetic polymorphism or from human manipulation. Biologically active variants of a periostin protein of the invention will have at least about 80%, 85%, 90%, 91%, 92%, 93%, 94%, 95%, 96%, 97%, 98%, 99% or more sequence identity to the amino acid sequence for the human periostin protein as determined by sequence alignment programs and parameters described elsewhere herein. A biologically active variant of a protein consistent with an embodiment of the invention may differ from that protein by as few as 1-15 amino acid residues, as few as 1-10, such as 6-10, as few as 5, as few as 4, 3, 2, or even 1 amino acid residue.

Periostin and Cardiomyocytes

Humans do not regenerate their hearts after injury; instead, the defect is replaced by fibrotic tissue. The inadequate regenerative response of injured human hearts contributes significantly to morbidity and mortality from cardiovascular diseases, such as myocardial infarction (MI). By contrast, lower vertebrates, such as newt and zebrafish, regenerate their hearts by cardiomyocyte proliferation. The invention discloses that cardiomyocyte proliferation, the cellular basis of regeneration, can be stimulated by periostin and biologically active fragments thereof. Periostin activates integrins, transmembrane proteins involved in cell adhesion and signaling, and thus stimulates specific signal transduction cascades in cardiomyocytes.

Periostin is absent from normal myocardium but present after myocardial injury; its function in the heart, however, is unknown. In one aspect of the invention, periostin and biologically active fragments thereof are cardioprotective. Manipulating periostin function after myocardial injury can enhance the regenerative capacity of mammalian hearts. The studies shown in the Examples provide the first detailed functional analysis of periostin in the recovery of the myocardium after injury, and provides new therapeutic approaches to heart failure.

Differentiated cardiomyocytes carry the pump function of the human heart. Loss of cardiomyocytes, such as after myocardial infarction, typically results in heart failure. Heart transplantation is currently the only biological myocardial replacement therapy. A small proportion of cardiomyocytes in adult hearts proliferates. Cardiomyocyte proliferation increases to 0.004% in the region bordering a myocardial infarction. This proliferative rate is not sufficient for myocardial regeneration.

Stem and progenitor cells can contribute to maintenance of the cardiomyocyte number in the adult mammalian heart. Although the stem cell population can maintain the balance between cardiomyocyte death and renewal, it is insufficient to mount a significant regenerative response after injury. Transplantation of bone marrow stem cells has variable effects on cardiac function in humans. Furthermore, regenerated myocardium derived from transplanted cells has been difficult to detect in vivo. Proliferating endogenous cardiomyocytes provide an alternative approach to regenerate myocardium.

In contrast to adult cardiomyocytes, fetal cardiomyocytes do proliferate. After birth, cardiomyocytes binucleate, downregulate cell cycle activators (e.g. cyclin A), up-regulate cell cycle inhibitors (e.g. retinoblastoma protein, Rb), and withdraw from the cell cycle. While modifications of intrinsic cell cycle regulators increase cell cycle activity of differentiated cardiomyocytes, extrinsic factors inducing cardiomyocyte proliferation are unknown.

Periostin, named after its expression in the periosteum, is a secreted protein of 834 amino acids (osteoblast specific factor (*Homo sapiens*) Accession No. NP_006466 (Seq ID. No. 1)). The expression of periostin during cardiac development in the myocardium and in the regions of the conotruncus provided the rationale to investigate its potential to promote cardiomyocyte proliferation. As shown in the Examples, periostin increases cell cycle activity and proliferation of differentiated cardiomyocytes. Local administration of periostin, and fragments thereof, in adult rat hearts induce cardiomyocyte DNA synthesis and cytokinesis in vivo. Long-term administration of periostin after experimental myocardial infarction improves cardiac function, reduces infarct size, and increases the number of cardiomyocytes. Thus, periostin can be applied to regenerate mammalian myocardium by stimulating proliferation of endogenous cardiomyocytes.

In some embodiments, the invention demonstrates that recombinant periostin, and biologically active fragments (such as periostin fragment polypeptide comprising fas1) delivered through the cardiac extracellular matrix, increases cardiomyocyte proliferation. Periostin induces cell cycle re-entry of differentiated mononucleated cardiomyocytes. Periostin stimulates integrins in cardiomyocytes leading to proliferation through both PI3-kinase/Akt and ERK1/2 dependent pathways. After experimental myocardial infarction, periostin induces cardiomyocyte cell cycle re-entry, reduces infarct size and fibrosis, and improves cardiac function. Periostin, and biologically active variants and fragments thereof, can be applied to enhance the regenerative capacity of adult mammalian hearts.

Periostin Structure and Function

Periostin is a secreted protein of 834 amino acids named after its expression in the periosteum and the periodontal ligament. The nascent periostin peptide contains a signal peptide and four fasciclin 1 (fas1) domains (Scheme 1). The fas1 domains are Scheme 1: Diagram of nascent Periostin peptide.

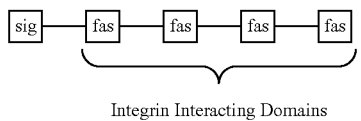

Integrin Interacting Domains
(sig, signal peptide; fas1, fasciclin 1)

interact with integrins. Periostin is expressed during myocardial development and re-expressed in adult life after myocardial injury and after vascular injury in rats, and after skeletal muscle injury and bone fracture in mice. Thus, periostin is a component of the response of different tissues to injury; however, the precise function remains unclear. The phenotype of the periostin knock-out mouse indicates that periostin has important functions in adult life. Periostin activates integrins in colon and ovarian carcinoma cells. Integrins connect cells to the extracellular matrix and function as receptors for extracellular signals, e.g. mechanical stress. Integrins are heterodimeric transmembranous receptors consisting of one α and one β subunit. To date, 18 α and 8 β subunits have been identified giving rise to 24 distinct subunit combinations (Hynes RO. Integrins: bidirectional, allosteric signaling machines. *Cell* 110:673-87. 2002). The integrin αβ heterodimers form an extracellular domain, which binds components of the extracellular matrix. With their intracellular domain integrins activate signaling pathways including the phosphoinositide 3-kinase/Akt (PI3-kinase/Akt) pathway and the extracellular signal-regulated kinase 1 and 2 (ERK1/2) pathway. Through the interaction with multiple signaling pathways, integrins control cell survival, proliferation, motility, and differentiation. The present invention shows that periostin activates integrins and protein kinases in cardiomyocytes.

The Extracellular Matrix and Integrins in the Heart

Through the interaction with integrins, components of the extracellular matrix control important cardiomyocyte functions, such as proliferation and survival. Fetal cardiomyocytes proliferate only when attached to the cell culture dish through β1-integrins. In vitro fetal mouse cardiomyocytes proliferate in response to an epicardial-derived extracellular factor, a response which can be disrupted at the level of the MEK1/ERK and PI3-kinase/Akt pathways.

Fetal and neonatal mammalian cardiomyocytes proliferate during development. Differentiated zebrafish and newt cardiomyocytes proliferate in vivo giving rise to remarkable regenerative capacity. The Examples show that adult mammalian cardiomyocytes proliferate in the presence of periostin. All observations were made in fully differentiated species with characteristic rod shape and striations, expressing cardiac contractile proteins (tropomyosin and troponin I) and cardiac (GATA-4) and myogenic markers (MEF-2). Thus, the postnatal proliferative quiescence of mammalian cardiomyocytes is not cell autonomous as addition of periostin and fragments thereof to the extracellular environment induces cardiomyocyte proliferation.

Transgenic overexpression of the cell cycle activators SV40 large T antigen, cyclin D2, and cyclin A2 increase cardiomyocyte cell cycle activity in vivo. Because these genetic modifications were present during development, inhibition of terminal differentiation of cardiomyocytes could not be excluded. Recombinant periostin was applied in adult animals, thus ruling out a developmental mechanism for adult cardiomyocyte proliferation.

Several molecular events lead to periostin-induced cardiomyocyte proliferation. Activation of integrins is required for periostin-dependent cardiomyocyte proliferation. Previous studies have shown that proliferation of fetal cardiomyocytes requires attachment to β1 integrins. Although the Examples suggest an important role for β3 integrins, periostin can activate other integrin subunit combinations. Two other components of the extracellular matrix, fibronectin and collagen, did not stimulate proliferation of postnatal cardiomyocytes. This underscores the high level of specificity of periostinstimulated cardiomyocyte proliferation. By contrast, receptor tyrosine kinases, such as FGF receptors, stimulate cardiomyocyte proliferation in vitro but induce cardiac hypertrophy in vivo.

It is notable that periostin-stimulated cardiomyocyte proliferation requires phosphorylation of ERK1/2 and Akt. Sustained activation of either pathway is sufficient to induce cardiac hypertrophy, but does not induce cardiomyocyte proliferation. The requirement of ERK1/2 activation for periostin-stimulated cardiomyocyte proliferation is consistent with a requirement of ERK2 for transit through the G2/M checkpoint of the cell cycle. The present data together with a recent report of increased cardiomyocyte cell cycling after overexpression of nuclear-targeted Akt suggest a previously uncharacterized function of Akt in cardiomyocyte proliferation.

Cardiomyocyte hypertrophy is the major mechanism to increase myocardial mass of the adult mammalian heart. Different extracellular factors, including ligands for G protein coupled receptors and receptor tyrosine kinases, induce cardiomyocyte hypertrophy. Extracellular factors inducing proliferation of differentiated cardiomyocytes in vivo are unknown. The Examples show that the signal transduction cascade consisting of extracellular periostin, integrins, and the ERK1/2 and the PI3-kinase/Akt pathways induces proliferation of postnatal cardiomyocytes. These findings have important medical implications for the treatment of heart failure, which remains a leading cause of morbidity and mortality. Periostin, periostin-derivatives, or small molecules that mimic its function, can be applied locally or systemically to induce myocardial regeneration via proliferation of endogenous differentiated cardiomyocytes.

Periostin Promotes Cardiac Regeneration

Figure 12:
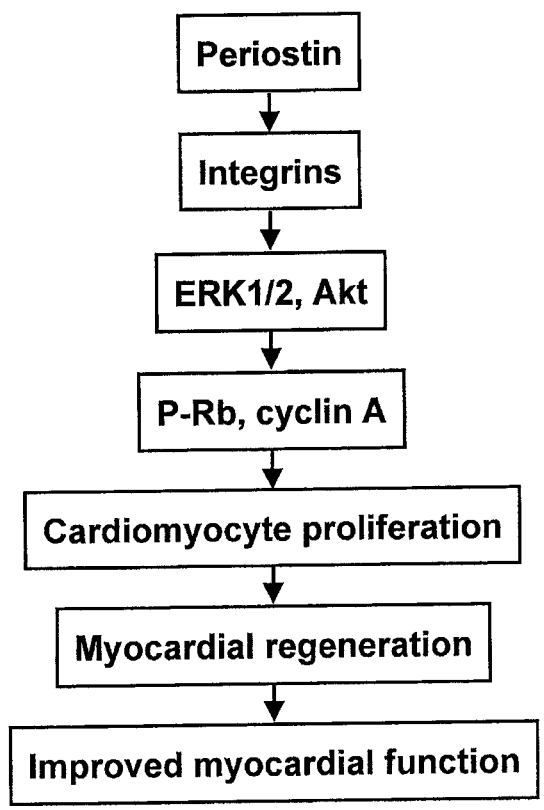
FIG. 12 depicts a schematic flow chart of periostin-induced cardiomyocyte regeneration.

The Examples show that periostin, a component of the extracellular matrix, and fragments thereof can induce myocardial regeneration by proliferating endogenous cardiomyocytes. Five lines of evidence support this conclusion. First, periostin induces DNA synthesis followed by cytokinesis in fully differentiated rod-shaped adult cardiomyocytes. Second, periostin stimulates cardiomyocyte proliferation in vitro. Third, periostin inactivates the cell cycle inhibitor retinoblastoma protein and increases levels of the cell cycle activator cyclin A in cardiomyocytes. Fourth, injection of recombinant periostin increases cardiomyocyte DNA synthesis and cytokinesis in the adult rat heart in vivo. Lastly, periostin-induced cardiomyocyte proliferation improves cardiac function and reduces scar size after experimental myocardial infarction. FIG. 12 depicts a schematic flow chart of periostin-induced cardiomyocyte regeneration.

Increased cardiomyocyte DNA synthesis in the border zone of a myocardial infarction suggests that differentiated cardiomyocytes re-enter the cell cycle. The Examples show that mononucleated rod-shaped cardiomyocytes, present in the adult mammalian heart, have proliferative potential. Proliferation of differentiated cardiomyocytes challenges the notion that their contractile apparatus prohibits cell division. Thus, the Examples demonstrate that differentiated cardiomyocytes, while maintaining the contractile apparatus, undergo DNA synthesis followed by cytokinesis. Sustained administration of periostin after myocardial infarction improves cardiac function and remodeling by at least two mechanisms: first, periostin increases cardiomyocyte cell cycle activity; second, periostin attenuates fibrosis and hypertrophy and increases angiogenesis. Periostin improves the maladaptive myocardial remodeling following myocardial infarction.

To induce cardiomyocyte proliferation, periostin activates $\alpha V \oplus 1/3/5$ integrins, which is consistent with the activation of $\alpha V \beta 1/3/5$ integrins by periostin in other systems. Interestingly, attachment to $\beta 1$ integrins is required for proliferation of fetal cardiomyocytes. The fas1 domains of periostin are sufficient to induce proliferation, suggesting that the integrin interaction domain lies within this region. This is in accord with the mapping of the integrin interaction sites to the fas1 domains of the structurally related protein $\beta igH3$. $\beta 1$ and $\beta 3$ integrins are upregulated in peri-infarct cardiomyocytes, endothelial cells, and fibroblasts. The cardiac-specific knockouts of $\beta 1$ or $\beta 3$ integrins show increased fibrosis, consistent with the finding that periostin, an agonist of $\beta 1$ and $\beta 3$ integrins, markedly decreases fibrosis after myocardial infarction and with increased extracellular matrix deposition in the heart valves of periostin knock-outs. $\alpha V \beta 1/3/5$ integrins are also involved in angiogenesis and periostin promotes tumor angiogenesis. Notably, periostin-treated hearts have a higher capillary density in the infarct and border zone.

Cell size, including cardiomyocyte size, is controlled by the PI3-kinase/Akt pathway. Periostin, like FGF, requires the PI3-kinase/Akt pathway to induce cardiomyocyte cell cycle re-entry, although activation of this pathway is not sufficient to induce proliferation. Extracellular periostin, in the absence of increased hemodynamic load, does not induce cardiomyocyte hypertrophy, but induces cell cycle re-entry and division. This is in contrast to two previous studies of cardiac overexpression of periostin or periostin-like factor under control of the CMV promoter. Liposomal gene delivery of periostin caused dilative cardiomyopathy without hypertrophy, whereas adenoviral gene delivery of periostin-like factor induced hypertrophy. This apparent discrepancy may be resolved when considering that normally cardiac fibroblasts express periostin and secrete it into the extracellular matrix, whereas delivery by gene transfer results in significant intracellular retention of the product.

The lower wall stress in periostin-treated hearts determined by catheterization decreases the hypertrophic drive after myocardial infarction, consistent with smaller cardiomyocyte cross-sectional area. Sustained cardiomyocyte replacement attenuated the increased wall stress after myocardial infarction, resulting in improved ventricular remodeling. Administration of periostin induced cell cycle re-entry in 1.4% of all cardiomyocytes in the infarct border zone without changing the rate of apoptosis. This proportion of cycling cardiomyocytes is comparable to that in cyclin D2 transgenes, combined p53 and p193 dominant-negative transgenes, after gene therapy with cyclin A2, and after administration of FGF with p38 MAP kinase block (Table 1). All of these interventions achieved significant functional improvement and infarct regression by inducing cardiomyocyte cell cycle activity.

TABLE 1

Morphometric and stereologic measurements 1 week after intracardiac injection of buffer (control), periostin (PN), or fibronectin (FN).

|  | control | PN | FN |
| --- | --- | --- | --- |
| Number of rats | 3 | 4 | 5 |
| LVFW myocardial volume (mm$^3$) | 218.4 ± 17.1 | 211.3 ± 12.3 | 224 ± 6 |
| LVFW CM nuclei ($10^{SS}$ per heart) | 10.2 ± 1.4 | 10.3 ± 0.3 | 10.7 ± 0.4 |
| LVFW BrdU-positive CM nuclei (per heart) | 595.2 ± 238.1 | 5411 ± 376** | 273.6 ± 42.8 |
| LVFW BrdU-positive CM nuclei (%) | 0.0064 ± 0.0033 | 0.051 ± 0.0021* | 0.002 ± 0.0004 |
| LVFW cytokineses (per heart) | 71.4 ± 41.2 | 821.4 ± 176.2 | 85.7 ± 14.3 |
| LVFW cytokineses (%) | 0.0007 ± 0.0004 | 0.008 ± 0.002** | 0.0007 ± 0.0002 |

LVFW, left ventricular free wall;
CM, cardiomyocyte;
data are represented as mean + SEM;
**$p < 0.01$ to control (Dunnett's multiple comparisons test).

The potential of resident or circulating cardiogenic stem cells to regenerate new cardiomyocytes after injury remains unknown. Stimulating proliferation of endogenous cardiomyocytes is an alternative approach to regenerate myocardium. Periostin, periostin-derivatives, or small molecules mimicking its function can be applied to induce myocardial regeneration by cardiomyocyte proliferation as described herein.

Increased cardiomyocyte DNA synthesis in the border zone of a myocardial infarction demonstrates that some differentiated cardiomyocytes reenter the cell cycle. The Examples show that differentiated mononucleated cardiomyocytes have proliferative potential. We have demonstrated that, after myocardial infarction, periostin-induced cycling of differentiated cardiomyocytes is associated with improved myocardial function and remodeling and with infarct regression.

We have shown that, to induce cardiomyocyte proliferation, periostin requires at least one integrin subunit selected from the group consisting of $\alpha_V$, an $\beta_1$, $\beta_3$ and $\beta_5$ integrin subunit. Integrins are upregulated in the infarct border zone, but have not been implicated in cell-cycle reentry of differentiated cardiomyocytes. Cardiac-specific knockout of $\beta_1$ or $\beta_3$ integrin results in increased fibrosis; this is consistent with our finding that periostin, a ligand of $\beta_1$ and $\beta_3$ integrins, markedly decreases fibrosis after myocardial infarction, and is also consistent with the increased extracellular matrix deposition in the heart valves of periostin knockout mice.

Recombinant extracellular periostin did not induce cardiomyopathy. This finding contrasts with two previous studies of cardiac overexpression of periostin or periostin-like factor. Liposomal gene delivery of periostin was found to cause dilated cardiomyopathy without hypertrophy (Katsuragi, N. et al. Periostin as a novel factor responsible for ventricular dilation. *Circulation* 110, 1806-1813 (2004)), whereas adenoviral gene delivery of periostin-like factor induced hypertrophy (Litvin, J. et al. *Cardiovasc. Pathol.* 15, 24-32 (2006)). This apparent discrepancy is due to the fact that cardiac fibroblasts usually express periostin and secrete it into the extracellular matrix, whereas delivery by gene transfer results in significant intracellular retention.

The lower wall stress in periostin-treated hearts determined by catheterization decreased the hypertrophic drive after myocardial infarction, consistent with the smaller cardiomyocyte cross-sectional area observed. Sustained cardiomyocyte replacement attenuated the increase in wall stress after myocardial infarction, resulting in improved ventricular remodeling. Administration of periostin induced cell-cycle reentry in 0.6-1% of all cardiomyocytes in the infarct border zone without affecting apoptosis. This proportion of cycling cardiomyocytes is comparable to that observed for cyclin D2 transgenes, for combined p53 and p193 dominant-negative transgenes, after gene therapy with cyclin A2, and after administration of FGF coupled with a p38 MAP kinase block (Pasumarthi, K. B., et al. *Circ. Res.* 96, 110-118 (2005); Nakajima, H., et al. *Circ. Res.* 94, 1606-1614 (2004); Woo, Y. J. et al. *Circulation* 114, 1206-1213 (2006); Engel, F. B., et al. *Proc. Natl. Acad. Sci. USA* 103, 15546.

The PI3K/Akt pathway controls cell size, including cardiomyocyte size. We found that periostin, like FGF, requires the PI3K/Akt pathway to induce cardiomyocyte cell-cycle reentry. Because of the myocardial protective effect of Akt, it is tempting to propose that periostin has an anti-apoptotic effect. However, our data show that periostin has no protective effect, suggesting that the pro-apoptotic signals dominate over possible protection through periostin-induced PI3K activation. After myocardial infarction, the epicardial delivery strategy may not effectively reach all cardiomyocytes in the ischemic area to induce functionally and structurally relevant myocardial protection.

Improvement of myocardial function can be achieved with circulating or resident stem cells, which requires their isolation, in vitro propagation, and transplantation. Although our results do not exclude the possibility that cardiogenic stem cells contribute to periostin-induced myocardial repair, we have shown that a subpopulation of differentiated cardiomyocytes has proliferative potential. Stimulating proliferation of endogenous cardiomyocytes with periostin, periostin derivatives, or mimetics provide an innovative approach to induce myocardial repair.

Uses of the Inventions

The invention is also applicable to tissue engineering where cells can be induced to proliferate by treatment with periostin, variants or fragments thereof (or such compositions together with growth factors) ex vivo. Following such treatment, the resulting tissue can be used for implantation or transplantation.

For example, in some embodiments, perostin, or biologically active variants or fragments thereof, are used as reagents in ex vivo applications. For example, perostin fragments are introduced into tissue or cells that are transplanted into a subject for therapeutic effect. The cells and/or tissue can be derived from an organism or subject that later receives the explant, or can be derived from another organism or subject prior to transplantation. The perostin compositions can be used to modulate the signaling pathway in the cells (i.e., cardiomyocytes), such that the cells or tissue obtain a desired phenotype or are able to perform a function (i.e., cardiomyocyte proliferation) when transplanted in vivo. In one embodiment, certain target cells from a patient are extracted. These extracted cells are contacted with perostin compositions. The cells are then reintroduced back into the same patient or other patients. Non-limiting examples of ex vivo applications include use in organ/tissue transplant, tissue grafting, or treatment of heart disease. Such ex vivo applications can also used to treat conditions associated with coronary and peripheral bypass graft failure, for example, such methods can be used in conjunction with peripheral vascular bypass graft surgery and coronary artery bypass graft surgery.

The compositions and methods of this invention have utility in research and drug development, as well as in surgery, tissue engineering, and organ transplantation. The present invention allows periostin, variants or fragments thereof to be delivered locally, both continuously and transiently, and systemically. The invention could be used to modify or reduce scar tissue around the heart, speed up healing, and enhance cardiac tissue generation. The methods and compositions of this invention provide the ability to successfully generate new tissue, augment organ function, and preserve the viability of impaired tissues, such as ischemic tissues. The present invention can enhance the viability of tissue.

Heart failure in humans begins with reduced myocardial contractility, which leads to reduced cardiac output. The methods and composition of the invention can be used to augment heart function. For example, the invention can be used to enhance growth of cardiomyocytes in an area of the heart that has been damaged or has become ischaemic. Heart diseases include, but are not limited to angina pectoris, myocardial infarction, and chronic ischemic heart disease.

Periostin, variants or fragments thereof, or a combination of one or more variants or fragments thereof, can be administered as compositions by various known methods, such as by injection (direct needle injection at the delivery site, subcutaneous, intravenous, etc.), oral administration, inhalation, transdermal application, catheter infusion, biolistic injectors, particle accelerators, Gelfoam, other commercially available depot materials, osmotic pumps, oral or suppositorial solid pharmaceutical formulations, decanting or topical applications during surgery, or aerosol delivery. Depending on the route of administration, the composition can be coated with a material to protect the compound from the action of acids and other natural conditions which can inactivate the compound. The composition can further include both the periostin compound and another agent, such as, but not limited to, a growth factor.

To administer the composition by other than parenteral administration, the composition can be coated with, or co-administer the composition with, a material to prevent its inactivation. For example, the composition can be administered to a subject in an appropriate diluent or in an appropriate carrier such as liposomes. Pharmaceutically acceptable diluents include saline and aqueous buffer solutions. Liposomes include water-in-oil-in-water CGF emulsions as well as conventional liposomes (Strejan et al., *J. Neuroimmunol.* 7:27 (1984)).

The composition containing at least one periostin protein, variants or fragments thereof can also be administered parenterally or intraperitoneally. Dispersions can also be prepared in glycerol, liquid polyethylene glycols, and mixtures thereof and in oils. Under ordinary conditions of storage and use, these preparations can contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene gloycol, and the like), suitable mixtures thereof, and vegetable oils. The proper fluidity can be maintained, for example, by the use of a coating such as licithin, by the maintenance of the required particle size in the case of dispersion and by the use of surfactants. Prevention of the action of microorganisms can be achieved by various antibacterial and antifungal agents. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the composition containing the periostin molecule, variants or fragments thereof in the required amount in an appropriate solvent with one or a combination of ingredients enumerated above, as required. Generally, dispersions are prepared by incorporating the composition into a sterile vehicle which contains a basic dispersion medium and the required other ingredients from those enumerated above.

When the composition containing the periostin composition is suitably protected, as described above, the composition can be orally administered, for example, with an inert diluent or an assimilable edible carrier. The composition and other ingredients can also be enclosed in a hard or soft shell gelatin capsule, compressed into tablets, or incorporated directly into the subject's diet. For oral therapeutic administration, the composition can be incorporated with excipients and used in the form of ingestible tablets, buccal tablets, troches, capsules, elixirs, suspensions, syrups, wafers, and the like. The percentage of the compositions and preparations can, of course, be varied. The amount of active compound in such therapeutically useful compositions is such that a suitable dosage will be obtained.

The tablets, troches, pills, capsules and the like can also contain a binder, an excipient, a lubricant, or a sweetening agent. Various other materials can be present as coatings or to otherwise modify the physical form of the dosage unit. For instance, tablets, pills, or capsules can be coated with shellac, sugar or both. Of course, any material used in preparing any dosage unit form should be pharmaceutically pure and substantially non-toxic in the amounts employed. As used herein "pharmaceutically acceptable carrier" includes any solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the active compound, use thereof in compositions of the invention is contemplated.

It is especially advantageous to formulate compositions of the invention in dosage unit form for ease of administration and uniformity of dosage. Dosage unit form as used herein refers to physically discrete units suited as unitary dosages for the subjects to be treated. Each dosage contains a predetermined quantity of active compound calculated to produce the desired therapeutic effect in association with the required pharmaceutical carrier. The specification for the novel dosage unit forms of the invention is dependent on the unique characteristics of the composition containing periostin, variants or fragments thereof, and the particular therapeutic effect to be achieved. Dosages are determined by reference to the usual dose and manner of administration of the ingredients.

One skilled in the art will appreciate further features and advantages of the invention based on the above-described embodiments. Accordingly, the invention is not to be limited by what has been particularly shown and described, nor by the examples set forth below. All publications and references cited herein are expressly incorporated herein by reference in their entirety.

EXAMPLES

The Examples show that extracellular periostin and biologically active fragments thereof induce cell cycle re-entry of differentiated mammalian cardiomyocytes. Periostin stimulates mononuclear cardiomyocytes, present in the adult mammalian heart, to undergo the full mitotic cell cycle. Periostin activates $\alpha V \beta 1/3/5$ integrins located in the cardiomyocyte cell membrane. Periostin-induced cardiomyocyte proliferation requires activation of the ERK1/2 and Akt signaling pathways. After myocardial infarction, recombinant periostin induces cardiomyocyte cell cycle re-entry, improves cardiac remodeling and function, reduces fibrosis and infarct size, and increases angiogenesis. Periostin and the pathway it regulates provides a new target for innovative strategies to treat heart failure.

I. Materials and Methods

Materials

Recombinant periostin, purified from HEK293 cells expressing the full-length human cDNA, was provided by Drs. Lan-Bo Chen and Meiru Dai (DFCI, Boston, Mass.) (Tai, I. T., Dai, M. & Chen, L. B. *Carcinogenesis* 26, 908-15 (2005)). The periostin fas1-only polypeptide was purified from *E. coli* and provided by BioVendor (Chandler, N.C.). Purity of >90% was established by SDS-PAGE and Coomassie staining. The periostin derivative consisting of 4 fas1 domains and purified from bacteria was provided by BioVendor (Chandler, N.C.). FGF1 was provided by R&D Systems (Minneapolis, Minn.). The integrin αV (RMV-7) and β1 (HMβ1-1) antibodies were provided by BioLegend (San Diego, Calif.). The integrin αVβ3 antibody (LM609) was kindly provided by Bing Luo (Center for Blood Research, Harvard Medical School) and the integrin α7 antibody (6A11) was provided by MBL (Woburn, Mass.). The integrin β3 (F11) and β5 (MAB1961Z), the aurora B kinase antibody, all chemical inhibitors, and type 1 rat collagen were provided by BD Biosciences (Franklin Lakes, N. J.). Rat fibronectin was from Biomedical Technologies (Stoughton, Mass.). The tropomyosin (CH1) and troponin T (CT3) antibodies were provided by the Developmental Studies Hybridoma Bank (Iowa City, Iowa). Antibodies against human periostin, 5-Bromo-2'-deoxyuridine (BrdU), phosphorylated histone H3, and Ki67 were provided by AbCam (Cambridge, Mass.). The Cyclin A, troponin I, vWF, and c-kit antibodies were provided by Santa Cruz Biotechnology (Santa Cruz, Calif.). The phospho-Rb, phospho-ERK1/2, and phospho-Akt antibodies were provided by Cell Signaling Technology (Danvers, Mass.). Fluorophore-conjugated secondary antibodies raised in goat were provided by Invitrogen.

Methods

Cardiomyocyte Isolation and Culture.

Primary neonatal rat ventricular cardiomyocytes were isolated using the Neomyts kit (Cellutron, Highland Park, N.J.), seeded at a density of $10^5$ cells/cm$^2$ onto gelatin-coated cover slips, stimulated for 3 days, and labeled with BrdU for the terminal 2 days. Primary adult ventricular cardiomyocytes were isolated from male (300 gm) Wistar rats (Charles River Laboratories) and maintained as described (Engel, F. B. et al. p38 MAP kinase inhibition enables proliferation of adult mammalian cardiomyocytes. *Genes Dev* 19, 1175-87 (2005)). Adult cardiomyocytes were stimulated daily for 9 days and labeled with 30 μM BrdU for the terminal 3 days. Cardiomyocytes were stimulated with periostin (500 ng/mL) and FGF (100 ng/mL). Inhibiting antibodies were added at a concentration of 10 μg/mL, cRGD at 10 μM, U0126 at 10 μM, PD98059 at 1 μM, LY294002 at 10 μM, and Wortmannin at 0.1 μM 30 min prior to stimulation. The vehicle used to dissolve factors or chemicals was added to unstimulated samples, which were then processed together with the test samples.

Immunofluorescence Microscopy.

DNA-synthesis was analyzed by visualization of BrdU uptake and cytokinesis was determined by detection of the cleavage furrow and the midbody with an antibody against aurora B kinase as described (Engel, F. B. et al. p38 MAP kinase inhibition enables proliferation of adult mammalian cardiomyocytes. Genes Dev 19, 1175-87 (2005)). Signals were visualized with secondary antibodies conjugated to Alexa 488, Alexa 546, Alexa 594, and Alexa 647 (Invitrogen). Nuclei were visualized with 4',6'-diamidino-2-phenylindole (DAPI, Invitrogen). For image acquisition, the value for γ was set at 1 and the lookup table settings were linear.

Cardiomyocyte Proliferation, Survival, and Apoptosis.

To determine cardiomyocyte proliferation, primary neonatal rat ventricular cardiomyocytes were quantified by counting with a hemocytometer after 3 days and 6 days of stimulation. To determine cardiomyocyte survival, primary neonatal rat ventricular cardiomyocytes were pre-treated with 500 ng/mL periostin or buffer for 30 min and then exposed to 0.5 μM doxycycline or 100 ng/mL TNFα for 24 hr and quantified by counting. Corresponding samples were stained with an antibody directed against tropomyosin as a cardiomyocyte marker to control for the percentage of differentiated cardiomyocytes. Apoptotic cardiomyocyte nuclei were determined after 24 hr with the In situ Cell Death Detection Kit (Roche, Indianapolis, Ind.) in combination with staining for troponin I.

Transcriptional Analysis.

RNA was prepared using Trizol reagent (Invitrogen) from neonatal rat ventricular cardiomyocytes after 72 hr of stimulation. Complementary DNA was synthesized from 2 μg RNA with the SuperScriptIII kit (Invitrogen) using oligo-dT primers. One μL cDNA was used as template for 20 μL PCR-reactions (95° C. for 2 min, 30 cycles of 95° C. for 2 min, 55° C. for 2 min, 72° C. for 5 min, followed by 72° C. for 10 min). Oligonucleotide primers used for detection of ANF were F: 5'-ATACAGTGCGGTGTCCAACA-3' (Seq ID No. 2), R: 5'-GGATCTTTTGCGATCTGCTC-3' (Seq ID No. 3), β-actin were F: 5'-GGAGAAGATTTGGCACCACAC-3' (Seq ID No. 4), R: 5'-CAGGGAGGAAGAGGATGCGGC-3' (Seq ID No. 5), 13-MHC were F: 5'-CTTCAACCACCA-CATGTTCG-3' (Seq ID No. 6), R: 5'-TACAGGTGCAT-CAGCTCCAG-3' (Seq ID No. 7); SMA were F: 5'-GTCGG-TATGGGTCAGAAGGA-3' (Seq ID No. 8), R: 5'-CTTTTCCAGGGAGGAGGAAG-3' (Seq ID No. 9); SERCA2 were F: 5'-ACTGGTGATGGTGTGAACGA-3' (Seq ID No. 10), R: 5'-TACGGGGACTCAAAGATTGC-3' (Seq ID No. 11), and for GAPDH: 5'-CTCATGACCA-CAGTCCATGC-3' (Seq ID No. 12), R: 5'-ATGTAGGCCAT-GAGGTCCAC-3' (Seq ID No. 13).

Western Blot.

Primary cardiomyocytes or heart tissue were lysed in 20 mM Tris (pH 7.5), 150 mM NaCl, 10 mM EDTA, 1 mM EGTA, 1% Triton X-100, 2.5 mm sodium pyrophosphate, 1 mM β-glycerol phosphate, 1 mM Na$_3$VO$_4$, 1 μg/ml, leupeptin, 1% NP-40 and 0.24 mg/mL Pefabloc SC (Roche) at 4° C. Protein concentrations were determined using the BCA assay (Pierce, Rockford, Ill.). Forty μg of cell lysate was separated on 10% SDS-polyacrylamide gels, blotted onto nitrocellulose membranes (Amersham, Piscataway, N. J.), which were then incubated with antibodies according to manufacturer's directions, followed by visualization with ECL reagent (Amersham).

Determination of Cardiomyocyte Ploidy.

Primary adult rat ventricular cardiomyocytes were incubated with 0.2 μg/mL Hoechst 33342 (Invitrogen) for 10 min. Nuclei were visualized with a mercury arc lamp and 4 random 20× microscopic fields were counted.

Cardiomyocyte Fate Tracking.

Primary adult rat ventricular cardiomyocytes were grown on gridded cover slips (Electron Microscopy Services, Ft. Washington, Pa.) and imaged in phase contrast at 10× magnification. Cardiomyocytes were transduced with an adenovirus leading to nuclear expression of histone2B-GFP (Shi, Q. & King, R. W. *Nature* 437, 1038-42 (2005)) under control of the chicken troponin T promoter (Ma, H., Sumbilla, C. M., Farrance, I. K., Klein, M. G. & Inesi, G. *Am J Physiol Cell Physiol* 286, C556-64 (2004)). Nuclei were visualized at 10× magnification with a mercury-arc lamp dimmed to 1.5% with a neutral density filter. Imaging and infection conditions did not adversely affect cell proliferation or viability (data not shown). Images of BrdU-positive cardiomyocytes were matched with the corresponding images from before stimulation. For quantification, differentiated cardiomyocytes were defined as striated rod-shaped structures with length/width ratio>1.5.

In Vitro Gene Transfer.

Type 5 recombinant adenoviruses were generated as described (He, T. C. et al. A simplified system for generating recombinant adenoviruses. *Proc Natl Acad Sci USA* 95, 2509-14 (1998)). The −268 bp chick troponin T promoter segment was used to control expression of the histone2B-GFP fusion construct (BD Biosciences). The CMV promoter was used for expression of the human PTEN cDNA. Adult rat ventricular cardiomyocytes were infected at multiplicity of infection of 20.

Determination of Cardiomyocyte Cell Cycle Activity In Vivo.

Experiments were performed in accordance with institutional guidelines of Massachusetts General Hospital. Injections and analyses were performed in a blinded fashion. Adult male Sprague-Dawley rats (300 gm, Charles River Laboratories) underwent thoracotomy and received intramyocardial injections of 50 µg of recombinant human periostin consisting of the fas1-4 domains, 50 µg of rat fibronectin, or 100 µL of 100 mM sodium acetate as a control (5 rats per group). The survival rate for this procedure was 80%. Injected periostin was confirmed by detection with a polyclonal antibody directed against human periostin (Abcam) and visualized by immunofluorescence microscopy. Intraperitoneal injections of BrdU (70 µmol/kg body weight) with a tissue half life of 2 hr were given every 48 hr, and rats were sacrificed after the third injection. Horizontal cryosections of 14 µm thickness spaced at 1 mm intervals were analyzed by laser scanning immunofluorescence microscopy. BrdU-positive cardiomyocyte nuclei and cytokineses were quantified on 16-20 sections per heart. Fibrosis and cardiomyocyte cross-sectional area were determined on 5 Masson's Trichrome-stained sections at the level of the injection at 40× magnification and quantified using the Metamorph software package (Molecular Devices Corp., Downingtown, Pa.).

Analysis of Myocardial Regeneration.

Horizontal cryosections of 14 µm thickness spaced at 1 mm intervals were analyzed. To determine infarct size, Masson's Trichrome-stained sections were analyzed at 1× magnification. The infarct border zone was defined as myocardial tissue within 0.5 mm of the fibrous scar tissue. Fibrosis and cardiomyocyte cross-sectional area were determined after staining with Masson's Trichrome at 10× and 40× magnification, respectively, and quantified using the Metamorph software package. BrdU-positive cardiac fibroblast nuclei were determined at 5 cross-sections per heart at the level of the myocardial infarction. Cardiomyocyte nuclei were counted using the optical dissector method (Howard, C. V. & Reed, M. *Unbiased Stereology: Three-Dimensional Measurement In Microscopy*, (BIOS Scientific Publishers, Oxford, 2005)) on troponin T and DAPI-stained sections in 32-60 random sample volumes of 84,500 µm per heart. BrdU-positive cardiomyocyte nuclei were quantified on 16-20 sections per heart. Cardiomyocyte apoptosis was determined using the In situ Cell Death Detection Kit (Roche) in combination with staining for troponin I. Capillaries, arterioles, and stem cells were detected with antibodies against von Willebrand factor (vWF), smooth muscle actin (SMA), and c-kit, respectively, and quantified at the level of the myocardial infarction.

Determination of Release Kinetics of Periostin from Gelfoam.

To develop a long-term delivery system for recombinant periostin, we determined if recombinant periostin associated with Gelfoam, a biodegradable biological scaffold. Gelfoam patches (Pfizer, New York, N.Y.) of 1 cm$^2$ diameter were loaded with 100 µg of recombinant human periostin and incubated with 1 mL of PBS at 37° C. with continuous agitation for 10 weeks. The supernatant was replaced every 2 weeks and the concentration of recombinant periostin in the supernatant was determined by Western blot using a polyclonal antibody directed against human periostin (Abeam). The diffusion range of recombinant periostin in myocardium was determined with a polyclonal antibody directed against human periostin followed by immunofluorescence microscopy. Presence of periostin in the myocardium was determined by Western blot using a polyclonal antibody directed against human periostin (Abeam).

Rat Model of Myocardial Infarction.

Adult male Sprague-Dawley rats (300 gm, Charles River Laboratories) underwent experimental myocardial infarction as described (del Monte, F. et al. Abrogation of ventricular arrhythmias in a model of ischemia and reperfusion by targeting myocardial calcium cycling. *Proc Natl Acad Sci USA* 101, 5622-7 (2004)). The survival rate was 67%. Gelfoam loaded with 100 µg of recombinant periostin or with buffer were applied over the myocardial infarction at the time of surgery. Rats received 3 intraperitoneal BrdU injections (70 µmol/kg body weight) with a half-life of 2 hr every 48 hr over a period of 7 days. Echocardiography and hemodynamic catheterization were performed as described (Prunier, F. et al. *Am J Physiol Heart Circ Physiol* (2006)).

Analysis of Myocardial Regeneration.

Horizontal cryosections of 14 µm thickness spaced at 1 mm intervals were analyzed. Masson's Trichrome-stained sections were analyzed at 10× magnification to determine infarct size (Pasumarthi, K. B., et al. *Circ Res* 96, 110-8 (2005)), defined as [coronal infarct perimeter (epicardial+endocardial)/total coronal perimeter (epicardial+endocardial)]×100 and thinning index (Engel, F. B., et al. *Proc Natl Acad Sci USA* 103, 15546-51 (2006)), defined as minimal infarct wall thickness/maximal septal wall thickness. The infarct border zone was defined as myocardial tissue within 0.5 mm of the fibrous scar tissue. Fibrosis was determined on 10× images of Masson's Trichrome stainings and quantified using the Metamorph software package (Molecular Devices Corp.). Cardiomyocyte cross-sectional area was determined after staining with Masson's Trichrome at 40× magnification and quantified using the Metamorph software package. BrdU-positive cardiac fibroblast nuclei were determined at 5 cross-sections per heart at the level of the myocardial infarction. Cardiomyocyte nuclei were counted on troponin T and DAPI-stained sections in 32-60 random sample volumes of 84,500 µm$^3$ per heart. BrdU-positive cardiomyocyte nuclei were quantified on 16-20 sections per heart. Capillaries and stem cells were detected with antibodies against von Willebrand factor (vWF) and c-kit, respectively, and quantified at 5 cross-sections per heart at the level of the myocardial infarction.

RNAi Suppression of Integrin αV and β1 subunits.

Oligomers directed against the coding sequences of αV and β1 integrin subunits were designed and subcloned into the mammalian expression vector pcDNA 6.2-GW/EmEGFP-miR (Block-IT Pol II miR RNAi Expression Vector Kit, Invitrogen, Table 2).

TABLE 2

Oligonucleotide sequences used for suppression of integrin subunits by RNAi.

| Gene name and ID | Construct | Oligonucleotide sequence |
|---|---|---|
| Rat integrin αV<br>XM_001068715 | #1 | 5'-TGCTGTTAGCTTGACACCTGCGTCT-<br>TGTTTTGGCCACT<br>GACTGACAAGACGCATGTCAAGCTAA-3'<br>(SEQ ID No. 14) |
| | #2 | 5'-TGCTGTTGAGTTCCAGCCT-<br>TCATCGGGTTTTGGCCACT<br>GACTGACCCGATGAACTGGAACTCAA-3'<br>(SEQ ID No. 15) |

TABLE 2-continued

Oligonucleotide sequences used for suppression of
integrin subunits by RNAi.

| Gene name and ID | Construct | Oligonucleotide sequence |
|---|---|---|
| | #3 | 5'-TGCTGTTTGCCTTGCTGAATGAACTTG-GTTTTGGCCACTGACTGACCAAGTTCACAGCAAGGCAA-3' (SEQ ID No. 16) |
| Rat integrin β1 NM_017022 | #1 | 5'-TGCTGATTCCTTGTAAACAGGCTG-GAGTTTTGGCCACTGACTGACTCCAGCCTTTACAAGGAAT-3' (SEQ ID No. 17) |
| | #2 | 5'-TGCTGTTTCCAGACAGTGTGCCCACT-GTTTTGGCCACTGACTGACAGTGGGCACTGTCTGGAAA-3' (SEQ ID No. 18) |
| | #3 | 5'-TGCTGTGAAGGACCACCTCTACTTCT-GTTTTGGCCACTGACTGACAGAAGTAGGTGGTCCTTCA-3' (SEQ ID No. 19) |

Two μg of plasmid DNA was electroporated (Amaxa Inc.) into $5 \times 10^6$ freshly isolated neonatal rat ventricular cardiomyocytes. Transduction efficiency determined by expression of GFP was 31.9±10.9% (n=6). Stimulation was begun 36 hr later and periostin-induced cardiomyocyte cell cycle re-entry was determined as described above. Transduced cardiomyocytes identified by GFP-expression were scored for analysis. Suppression of integrin protein levels was determined by immunofluorescence microscopy using antibodies against integrin αV (Chemicon) and against β1 (BD Pharmingen).

Statistical Analysis.

Observations were quantified by 2 independent investigators (B. K. and S. A.) in a blinded fashion. Numeric data are presented as means±SEM. Statistical significance was determined using two-tailed t-test and ANOVA. The value α was set at 0.05 for statistical significance.

II. Periostin Stimulates Cell Cycle Reentry and Cell Division of Differentiated Adult Ventricular Cardiomyocytes In Vitro.

This Example demonstrates that periostin stimulates cell cycle reentry and cell division of differentiated adult ventricular cardiomyocytes in vitro. Periostin was identified in a screen of candidate compounds for induction of DNA synthesis in primary neonatal cardiomyocytes. To determine whether periostin activates the cell cycle and proliferation of fully differentiated adult ventricular cardiomyocytes, we tracked the fate of individual cardiomyocytes in vitro. Primary adult rat ventricular cardiomyocytes uniformly displayed rod-shaped phenotype, characteristic of full differentiation (data not shown). DNA synthesis was determined by uptake of the thymidine analog BrdU. Cardiomyocytes were identified by expression of the cardiac contractile protein tropomyosin and by expression of the cardiac transcription factor GATA-4 (data not shown). Using the in vitro tracking method, we matched images of cardiomyocytes in S-phase with the corresponding images from before stimulation. Analysis of sets of phase contrast images and immunofluorescence images revealed that fully differentiated rodshaped cardiomyocytes undergo DNA synthesis. Primary neonatal rat ventricular cardiomyocytes were stimulated for 3 days and analyzed by immunofluorescence microscopy (data not shown). Periostin stimulated a 14-fold increase of cardiomyocyte DNA synthesis to 1.1±0.2% (FIG. 1a). FGF, a known stimulus of DNA synthesis in adult cardiomyocytes in vitro, induced DNA synthesis in 1.3±0.6%.

Cytokinesis was determined by visualization of the aurora B kinase, located at the contractile ring at the site of cytoplasmic separation and required for cytokinesis. Rod-shaped cardiomyocytes underwent cytokinesis after stimulation with periostin or FGF (FIG. 1b). Nonstimulated cardiomyocytes did not progress into cytokinesis. We detected aurora B kinase after dissociation from the midbody, characteristic for completion of cytokinesis (FIG. 1b). Periostin stimulated cytokinesis in 0.5±0.2% and FGF in 0.3±0.1% of all differentiated cardiomyocytes (FIG. 1b). We conclude that periostin stimulates DNA synthesis and cytokinesis in fully differentiated adult cardiomyocytes.

Most adult mammalian cardiomyocytes are binucleated. One possible explanation of our results is breakdown of binucleated cardiomyocytes into mononucleated cardiomyocytes, without prior DNA synthesis. To determine whether DNA synthesis preceded cytokinesis, the time-course of periostin-stimulated DNA synthesis and cytokinesis was determined. Periostin induced cardiomyocyte DNA synthesis beginning after 3 days. In contrast, cytokinesis was not detected before 6 days of stimulation. If periostin-stimulated DNA synthesis preceded cytokinesis, cardiomyocytes in cytokinesis should be BrdU positive. We tested this hypothesis by visualizing the contractile ring in BrdU-labeled cardiomyocytes (FIG. 1c). Thus, periostin induces cardiomyocytes to reenter the cell cycle from S-phase and to complete the cell cycle with cytokinesis.

III. Recombinant Periostin and Fragments Thereof Stimulates Proliferation of Neonatal Cardiomyocytes.

This Example demonstrates that recombinant periostin stimulates proliferation of neonatal cardiomyocytes. The presence of periostin in the developing myocardium prompted us to investigate if it induces proliferation of primary neonatal rat ventricular cardiomyocytes. Recombinant human periostin at a concentration of 500 ng/mL induced DNA synthesis in 35±5% of cardiomyocytes, a 5-fold increase over non-stimulated cardiomyocytes (FIG. 1a). Periostin induced a 12-fold increase of cardiomyocyte mitoses and 8-fold increase of cytokineses (FIG. 1a). Co-stimulation with FGF, a factor known to induce cardiomyocyte DNA synthesis, had an additive effect (FIG. 1b). Periostin increased the population of proliferating cardiomyocytes, determined by expression of the marker Ki-67, by 4-fold, similar to FGF (FIG. 1c). To test whether periostin-stimulated cell cycle activity results in proliferation, we determined the number of cardiomyocytes before and after stimulation. Periostin induced a 3.6-fold increase of cardiomyocyte proliferation after 3 days and a 4.2-fold increase after 6 days (FIG. 1d). Inactivation of the cell cycle inhibitor retinoblastoma protein (Rb) by phosphorylation is necessary for release of the G1/S checkpoint of the cell cycle (Pasumarthi, K. B. & Field, L. J. Cardiomyocyte cell cycle regulation. *Circ Res* 90, 1044-54 (2002)). Periostin increased the number of cardiomyocytes with detectable levels of phosphorylated Rb by 12-fold (FIG. 1e). Cardiomyocytes expressing cyclin A, required for transition of the G1/S and G2/M checkpoints (Rape, M. & Kirschner, M. W. Autonomous regulation of the anaphase-promoting complex couples mitosis to S-phase entry. *Nature* 432, 588-95 (2004)), were increased 11-fold after stimulation with periostin (FIG. 1f). These data indicate that periostin stimulates all phases of the cell cycle leading to proliferation of neonatal cardiomyocytes.

IV. Specificity of Periostin and Fragments Thereof for Inducing Cardiomyocyte Proliferation.

Figure 2:
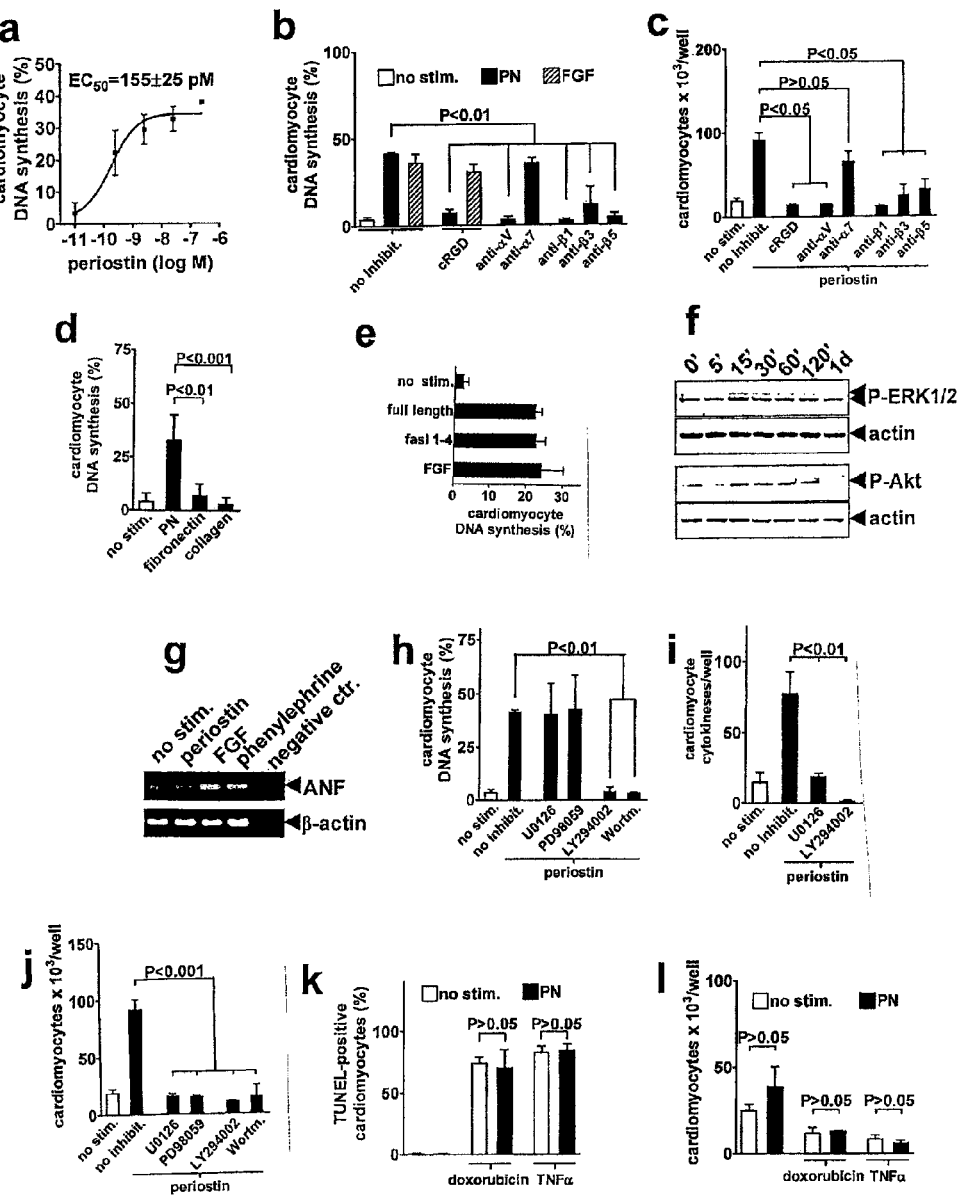
FIG. 2a is a graph showing primary neonatal rat ventricular cardiomyocytes DNA synthesis in the presence of increasing concentrations of periostin.
FIG. 2b is a graph showing periostin-induced DNA synthesis of neonatal rat ventricular cardiomyocytes blocked by cyclic RGD peptide (cRGD) (10 µM) and integrin blocking antibodies (10 µg/mL)
FIG. 2c is a graph showing periostin-induced proliferation of neonatal rat ventricular cardiomyocytes blocked by cRGD (10 µM) and integrin blocking antibodies (10 µg/mL)
FIG. 2d is a graph of cardiomyocyte DNA synthesis in the presence of periostin, fibronectin, or collagen type I.
FIG. 2e is a graph of primary neonatal rat ventricular cardiomyocytes DNA synthesis following stimulation with recombinant full length periostin, fast 1-4 domains, and FGF.
FIG. 2f is a Western blot after stimulation of primary neonatal rat ventricular cardiomyocytes with periostin for the duration indicated at the top followed and visualization of ERK1/2 and Akt phosphorylation, and membranes re-probed with an antiserum against actin (lower panel)
FIG. 2g shows transcription of atrial natriuretic factor determined by RT-PCR with β-actin as positive control.
FIG. 2h is a graph showing primary neonatal rat ventricular cardiomyocyte DNA synthesis inhibited by ERK inhibitors U0126 (10 µM) and PD98059 (1 µM) or PI3-kinase inhibitors LY294002 (10 µM) and Wortmannin (0.1 µM)
FIG. 2i is a graph showing primary neonatal rat ventricular cardiomyocytes cytokinesis inhibited by ERK inhibitors U0126 (10 µM) and PD98059 (1 µM) or PI3-kinase inhibitors LY294002 (10 µM) and Wortmannin (0.1 µM)
FIG. 2j is a graph showing primary neonatal rat ventricular cardiomyocyte proliferation inhibited by ERK inhibitors U0126 (10 µM) and PD98059 (1 µM) or PI3-kinase inhibitors LY294002 (10 µM) and Wortmannin (0.1 µM)
FIG. 2k is a graph showing primary neonatal rat ventricular cardiomyocyte apoptosis by TUNEL assay with and without stimulation by periostin (PN)
FIG. 2l is a graph showing primary neonatal rat ventricular cardiomyocyte survival following doxorubicin and TNF-α-induced cardiomyocyte death with and without stimulation by periostin (PN)

To rule out the possibility that cardiomyocyte cell cycle activity was due to a non-protein impurity, boiled periostin was used in control experiments, which did not activate the cardiomyocyte cell cycle (data not shown). Periostin induced cardiomyocyte DNA synthesis with half-maximal stimulation at 155±25 nM, indicating a highly specific interaction of periostin with its receptor (FIG. 2a). Because periostin activates integrins in other systems, we determined if blocking integrins would inhibit periostin-stimulated cardiomyocyte cell cycle activity. Cyclic Arg-Gly-Asp (cRGD), which blocks the activation site of a broad range of integrins, inhibited periostin-stimulated DNA synthesis, but not FGF-stimulated DNA synthesis (FIG. 2b). Blocking antibodies against αV, β1, β3, and β5 integrins inhibited periostin-stimulated DNA synthesis (FIG. 2b) and proliferation (FIG. 2c). Blocking α7 integrins had no effect. Fibronectin and collagen, known to activate integrins, did not induce DNA synthesis (FIG. 2d). To determine if the alternatively spliced carboxy-terminus of periostin is required for cell cycle re-entry, we compared full-length periostin with a derivative comprised of 4 fas1 domains. Full-length periostin, with a molecular weight of 90 kDa, and the variant consisting of the 4 fas1 domains, with a molecular weight of 75 kDa, stimulated DNA synthesis as effectively as FGF (FIG. 1e). In conclusion, the periostin fas1 domain-only polypeptide is sufficient to stimulate cardiomyocyte cell cycle re-entry.

V. ERK1/2 and Akt are Required for Periostin-Induced Cardiomyocyte Proliferation.

Integrins activate the ERK1/2 and PI3-kinase/Akt pathways of the mitogen activated protein kinase (MAPK) cascade (Miranti, C. K. & Brugge, J. S. Sensing the environment: a historical perspective on integrin signal transduction. *Nat Cell Biol* 4, E83-90 (2002)). Periostin activated ERK1/2 and Akt in neonatal cardiomyocytes (FIG. 2f). Because the ERK1/2 and PI3-kinase/Akt pathways control cardiomyocyte size and hypertrophy, we determined if periostin induces the hypertrophic gene program. Notably, periostin did not induce transcription of atrial natriuretic factor (ANF), a marker for cardiomyocyte hypertrophy (Sadoshima, J. & Izumo, S. *Annu Rev Physiol* 59, 551-71 (1997)) (FIG. 2g). By contrast, the known hypertrophic stimuli FGF and phenylephrine both induced ANF (FIG. 2g).

To determine if periostin-dependent ERK1/2 and PI3-kinase/Akt activation were linked to cardiomyocyte cell cycle activity, ERK1/2 activation by MEK1/2 was blocked with the compounds U0126 (10 µM) and PD98059 (1 µM) and Akt activation by PI3-kinase was blocked with LY294002 (10 µM) and Wortmannin (0.1 µM). Periostin-stimulated DNA synthesis was inhibited only by blocking Akt activation (FIG. 2h). By contrast, cardiomyocyte cytokinesis (FIG. 2i) and proliferation (FIG. 2j) were inhibited by both, ERK1/2 and Akt inhibition. In summary, ERK1/2 is not required for periostin-induced cardiomyocyte cell cycle re-entry, but periostin must activate both pathways to complete the cell cycle and induce proliferation, suggesting specific functions for distinct cell cycle events. Because periostin augments cancer cell survival, we tested if periostin enhances cardiomyocyte survival. Baseline and induced cardiomyocyte apoptosis (FIG. 2k) and survival (FIG. 2l) were not affected by periostin.

VI. Periostin and Fragments Thereof Stimulate Cell Cycle Re-Entry and Cell Division of Differentiated Cardiomyocytes in Vitro.

Figure 3:
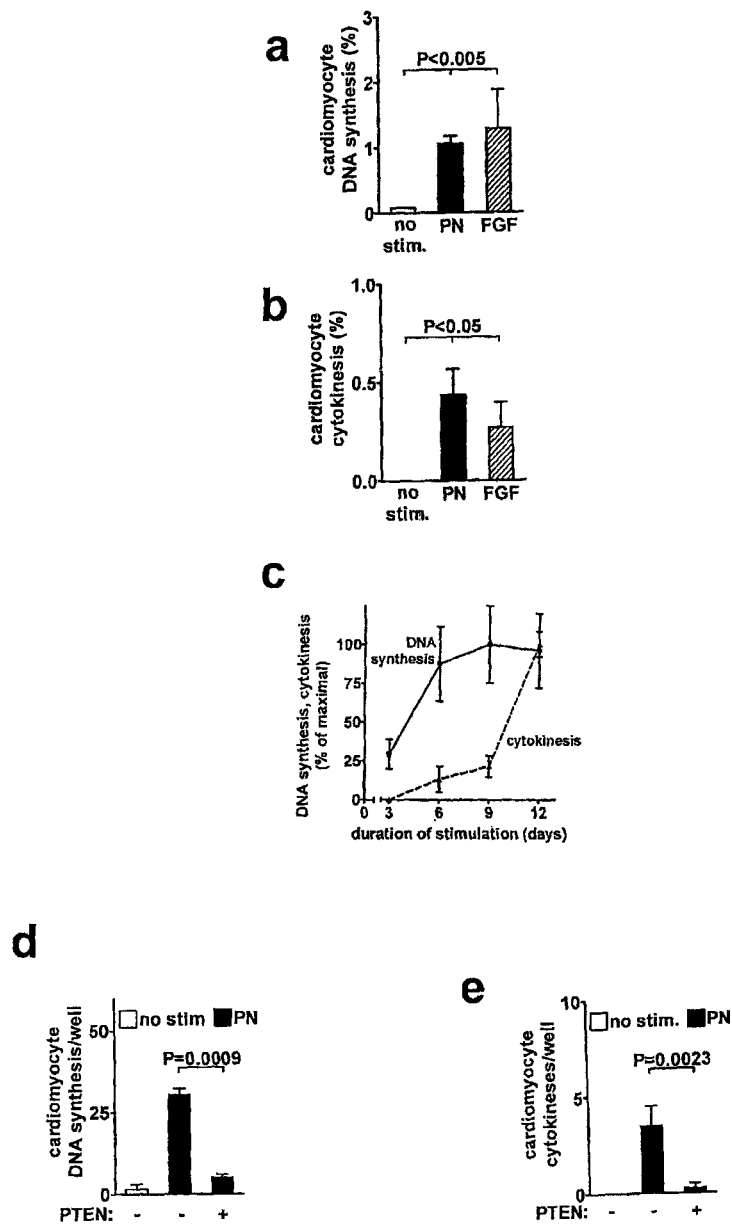
FIG. 3a shows that periostin increases DNA synthesis of differentiated mononucleated primary adult rat ventricular cardiomyocytes in S-phase retaining expression of tropomyosin following stimulation with periostin for 9 days and labeling with BrdU for the terminal 3 days.
FIG. 3b shows that periostin increases cytokinesis of differentiated mononucleated primary adult rat ventricular cardiomyocytes in cytokinesis expressing troponin I following stimulation with periostin for 9 days and labeling with BrdU for the terminal 3 days.
FIG. 3c is a graph of DNA synthesis and cytokinesis of primary adult rat ventricular cardiomyocytes stimulated with periostin, BrdU was added for the terminal 3 days, and DNA synthesis and cytokinesis analyzed at the indicated times.
FIG. 3d is a graph of DNA synthesis of cardiomyocytes that were transduced with PTEN, stimulated with periostin, and cell cycle activity was determined by immunofluorescence microscopy.
FIG. 3e is a graph of cytokinesis of cardiomyocytes that were transduced with PTEN, stimulated with periostin, and cell cycle activity was determined by immunofluorescence microscopy or fibronectin.

This Example shows that periostin and fragments thereof induce cell cycle re-entry of differentiated cardiomyocytes. Primary adult rat ventricular cardiomyocytes uniformly displayed a rod-shaped phenotype, characteristic of terminal differentiation (FIG. 3a, b). After 9 days of stimulation with 500 ng/mL periostin and addition of BrdU for the terminal 3 days, DNA synthesis was determined. Tracking the fate of individual rod-shaped cardiomyocytes revealed that they undergo DNA synthesis while expressing the cardiac contractile protein tropomyosin. Periostin induced a 14-fold increase of cardiomyocyte DNA synthesis to 1.1±0.2%, similar to FGF, known to promote cell cycle re-entry of differentiated cardiomyocytes (FIG. 3a).

In cardiomyocytes, cytokinesis is not obligatory. We detected cardiomyocyte cytokineses by visualizing aurora B kinase, located at the contractile ring at the site of cytoplasmic separation and required for cytokinesis. Nonstimulated cardiomyocytes did not progress into cytokinesis. After stimulation with periostin, we detected aurora B kinase after dissociation from the midbody, characteristic for completion of cytokinesis (FIG. 3b). Periostin stimulated cytokinesis in 0.5±0.2% of cardiomyocytes, similar to FGF (FIG. 3b). In conclusion, extracellular periostin re-activates the cell cycle and induces division in terminally differentiated cardiomyocytes.

Because most adult mammalian cardiomyocytes are binucleated (Soonpaa, M. H., Kim, K. K., Pajak, L., Franklin, M. & Field, L. J. Cardiomyocyte DNA synthesis and binucleation during murine development. *Am J Physiol* 271, H2183-9 (1996)), a possible origin of cardiomyocyte cytokinesis is breakdown of binucleated cardiomyocytes into mononucleated cardiomyocytes, without prior DNA synthesis. Periostin-induced cardiomyocyte DNA synthesis began after 3 days, whereas cytokinesis was not detected before 6 days (FIG. 3c). If periostin-stimulated DNA synthesis preceded cytokinesis, then cardiomyocytes in cytokinesis should be BrdU-positive. We detected BrdU-labeled nuclei in 100% of cardiomyocyte cytokineses (N=15, data not shown). Using a third-generation lentivirus (Rubinson, D. A. et al. *Nat. Genet.* 33, 401-406 (2003)), we genetically labeled autologous cardiac fibroblasts to exclude the possibility that their fusion with differentiated cardiomyocytes induced cell-cycle reentry. Cardiac fibroblasts form cell-cell contacts with differentiated cardiomyocytes, but do not fuse to induce cell cycle re-entry in vitro. Isolated adult rat ventricular cardiomyocytes were co-cultured for 9 days with autologous cardiac fibroblasts genetically labeled by infection with a third generation lentivirus directing expression of GFP under control of the CMV promoter. Cell-cell contact between cardiomyocytes and cardiac fibroblasts without fusion was observed. In conclusion, periostin induces the full mitotic cell cycle in differentiated cardiomyocytes.

Hoechst 33342 staining showed that 7.3±1.7% (N=6) of rod-shaped cardiomyocytes were mononucleated, consistent with prior reports. To test if mono- and binucleated cardiomyocytes have the same proliferative potential, we visualized expression of nuclear histone-2B tagged with green fluorescent protein (H2B-GFP) and analyzed cell cycle activity after 6 days. After 3 days of BrdU labeling, 1.7±0.3% of all mononucleated cardiomyocytes were BrdU-positive. By contrast, only 0.2±0.03% of binucleated cardiomyocytes were BrdU positive (P≤0.001). In conclusion, mononucleated rod-shaped cardiomyocytes, present in the normal adult heart, have proliferative potential. Differentiated mononucleated cardiomyocytes have higher proliferative potential than do binucleated cardiomyocytes.

The PI3-kinase/Akt pathway controls the size of differentiated cardiomyocytes. To determine if this pathway is required for cell cycle re-entry, we transduced the PI3-kinase inhibitor PTEN (Crackower, M. A. et al. Regulation of myocardial contractility and cell size by distinct PI3K-PTEN signaling pathways. *Cell* 110, 737-49 (2002)). Expression of PTEN abolished periostin-stimulated cardiomyocyte DNA synthesis and cytokinesis (FIG. 3d&e), indicating that periostin releases the proliferative potential of differentiated cardiomyocytes in a PI3-kinase/Akt dependent mechanism.

Figure 5:
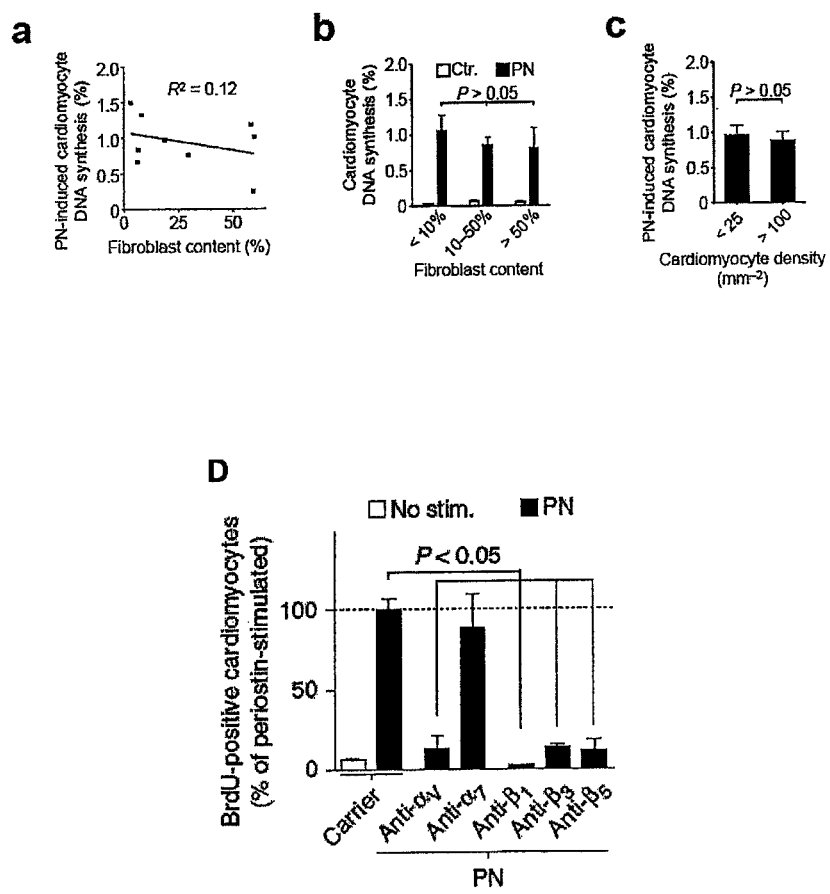
FIG. 5a is a graph of periostin-induced cardiomyocyte DNA synthesis determined by immunofluorescence microscopy versus percentage of fibroblasts present in the same specimen when isolated adult rat ventricular cardiomyocytes were seeded with different amounts of autologous cardiac fibroblasts.
FIG. 5b is a graph of cardiomyocyte cell cycle re-entry in the absence and presence of periostin and different percentages of autologous cardiac fibroblasts.
FIG. 5c is a graph of periostin-induced cardiomyocyte DNA synthesis of isolated adult rat ventricular cardiomyocytes seeded at different densities and periostin-induced cardiomyocyte cell cycle re-entry determined by immunofluorescence microscopy (Ctr., control; PN, periostin)
FIG. 5d is a graph of DNA synthesis in adult rat ventricular cardiomyocytes in the presence of different integrin blocking antibodies (10 mg/ml). n=4.

Cardiomyocyte cycling requires integrins and PI3K Periostin-induced cardiomyocyte cell-cycle reentry was concentration dependent (FIG. 2A) and did not correlate with the abundance of cardiac fibroblasts (FIG. 5a-c), suggesting that periostin has a direct effect on cardiomyocytes. As shown in FIG. 5a-c, periostin-induced cardiomyocyte cell cycle re-entry does not correlate with abundance of cardiac fibroblasts. Assays were performed in isolated adult rat ventricular cardiomyocytes. Isolated adult rat ventricular cardiomyocytes were seeded with different amounts of autologous cardiac fibroblasts. Periostin-induced cardiomyocyte DNA synthesis was determined by immunofluorescence microscopy. Regression of periostin-induced cardiomyocyte DNA synthesis and percentage of fibroblasts present in the same specimen shows lack of correlation (FIG. 5a). Cardiomyocyte cell cycle re-entry in the absence and presence of periostin and different percentages of autologous cardiac fibroblasts (FIG. 5b). Isolated adult rat ventricular cardiomyocytes were seeded at different densities and periostin-induced cardiomyocyte cell cycle re-entry was determined by immunofluorescence microscopy (FIG. 5c).

Figure 6:
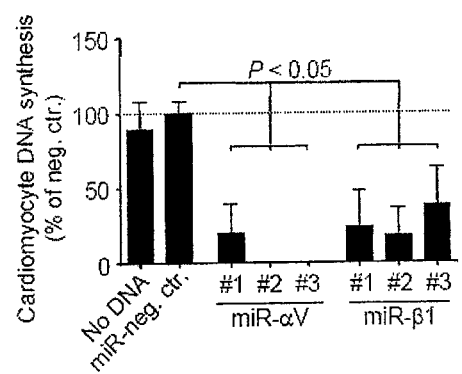
FIG. 6 is a graph of quantification of periostin-induced BrdU-uptake after transduction of neonatal ventricular cardiomyocytes with different targeting constructs (microRNA (miR) sequences targeting integrin αV and β1.

Integrins can function as periostin receptors in cardiomyocytes. We therefore determined whether blocking specific integrin subunits would inhibit periostin-stimulated cardiomyocyte cell-cycle activity. Antibodies specific to $\alpha_V$, $\beta_1$, $\beta_3$ and $\beta_5$ integrins inhibited periostinstimulated DNA synthesis in differentiated cardiomyocytes, whereas blocking $\alpha_7$ integrin had no effect (FIG. 5d). Reducing the expression of integrin $\alpha_V$ or $\beta_1$ by RNA-mediated interference (RNAi) inhibited periostin-induced cell-cycle reentry in neonatal cardiomyocytes (FIG. 2b, 2c, 6). Periostin requires integrin $\alpha_V$ and a $\beta_1$, $\beta_3$ or $\beta_5$ subunit to induce cardiomyocyte cellcycle reentry.

Periostin-stimulated proliferation of neonatal cardiomyocytes requires integrins. Periostin-induced DNA synthesis (FIG. 2b) and proliferation (FIG. 2c) of neonatal ventricular cardiomyocytes is blocked by cRGD (10 μM) and integrin blocking antibodies (10 μg/mL). Suppression of periostin-induced cardiomyocyte BrdU uptake with microRNA (miR) sequences targeting integrin $\alpha_V$ and $\beta_1$ was analyzed (not shown). FIG. 6 shows quantification of periostin-induced BrdU-uptake after transduction with different targeting constructs. Dotted line indicates periostin-induced cardiomyocyte DNA synthesis in the presence of miR-negative control. Suppression of integrin $\alpha_V$ and $\beta_1$ expression by miR constructs was visualized (not shown). Statistical significance tested with ANOVA.

Figure 7A:
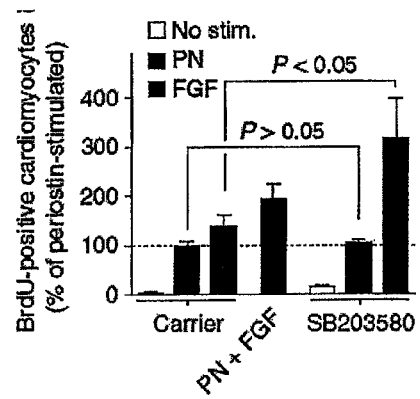
FIG. 7a is a graph showing the effect of FGF addition (100 ng/ml) and p38 MAP kinase inhibition (10 mM SB203580) on periostin-induced DNA synthesis in adult rat ventricular cardiomyocytes (n=3)

FGF-induced cardiomyocyte cell-cycle reentry is enhanced by concurrently inhibiting p38 mitogen-activated protein (MAP) kinase. We therefore determined whether periostin-induced cardiomyocyte cell-cycle reentry could be augmented by adding FGF (100 ng/ml) or by inhibiting p38 MAP kinase with the compound SB203580 (5 mM). Whereas adding FGF increased periostin-induced cardiomyocyte DNA synthesis, inhibiting p38 MAP kinase had no additional effect (FIG. 7A).

Figure 7B:
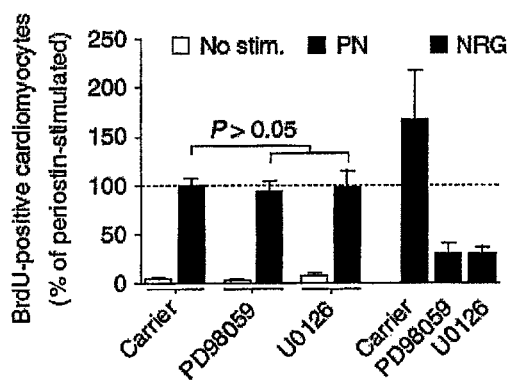
FIG. 7b is a graph showing that chemical inhibition of the ERK1/2 pathway with PD98059 (1 mM) and U0126 (10 mM) did not block periostin-induced DNA synthesis (n=4)
Figures 7C, 7D:
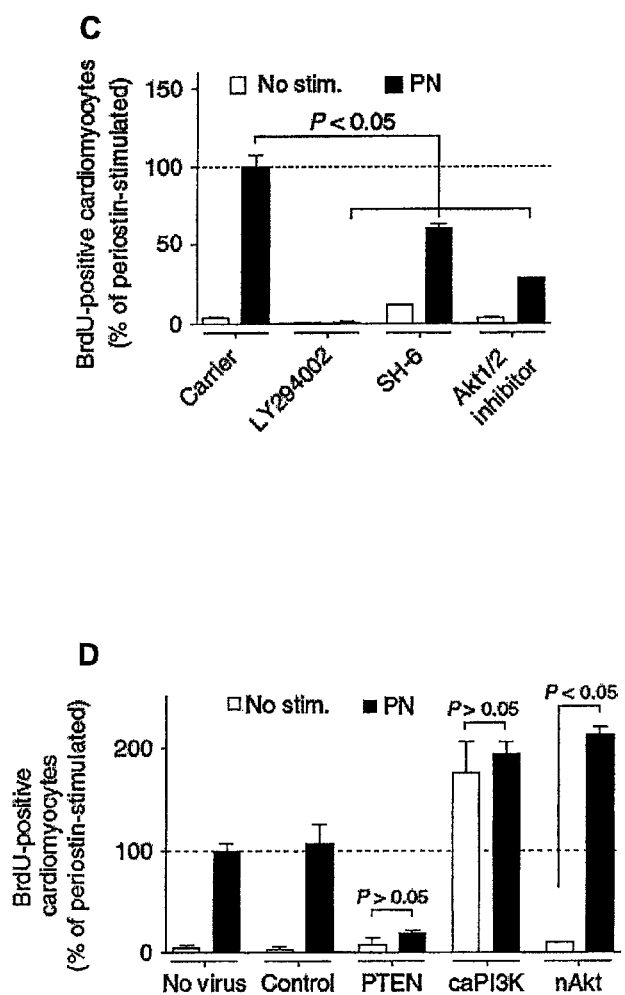
FIG. 7c is a graph showing that chemical inhibition of PI3K with LY294002 (10 mM) and Akt with SH-6 (10 mM) or Akt1/2 inhibitor (1 mM) reduced periostin-induced DNA synthesis (n=4)
FIG. 7d is a graph showing cardiomyocyte DNA synthesis after modification of PI3K and Akt signaling by adenoviral transduction with control (lacZ, GFP), PTEN, constitutively active PI3K (caPI3K), and nuclear targeted Akt (nAkt) (n=5)

Integrins activate the extracellular signal-regulated kinases 1 and 2 (ERK1/2) and PI3K pathways of the MAP kinase cascade24. In neonatal cardiomyocytes, compounds blocking the ERK1/2 pathway did not inhibit periostin-induced cell-cycle reentry. In differentiated cardiomyocytes, blocking the ERK1/2 pathway with the compounds PD98059 (1 mM) and U0126 (10 mM) did not reduce periostin-induced cell-cycle reentry, whereas under the same conditions they inhibited neuregulin-induced cell-cycle reentry (FIG. 7B). These results indicate that the ERK1/2 pathway is not required for periostin-induced cell-cycle reentry of differentiated cardiomyocytes. LY294002 (10 mM) fully inhibited periostin-induced cardiomyocyte cell-cycle reentry, however, suggesting that the PI3K pathway is involved (FIG. 7C). The protein kinase Akt is an important downstream target of PI3K in cardiomyocytes25. Inhibition of Akt signaling with two different compounds, SH-6 (10 mM) or an Akt1/2 inhibitor (1 mM), reduced periostin-induced cardiomyocyte cell-cycle reentry (FIG. 7C).

To confirm these results, we used adenoviral transduction to express regulators of the PI3K pathway. Activation of the PI3K cascade was functionally disrupted by transducing the bifunctional phosphatase PTEN26. Expression of PTEN abolished periostin-stimulated DNA synthesis in cardiomyocytes (FIG. 7D), indicating that periostin releases the proliferative potential of differentiated cardiomyocytes in a PI3K-dependent mechanism. Transduction of a constitutively active form of PI3K increased cardiomyocyte DNA synthesis in the absence of periostin (FIG. 7D), and adding periostin did not further augment cardiomyocyte cell-cycle reentry (FIG. 7D). Cardiomyocyte cell-cycle reentry induced by constitutively active PI3K was associated with abnormally shaped nuclei (data not shown). Whereas constitutively active Akt induces cardiomyocyte hypertrophy, nuclear targeted Akt is associated with cardiomyocyte proliferation. Accordingly, we transduced nuclear targeted Akt, which had no effect on cardiomyocyte DNA synthesis in the absence of periostin. In the presence of periostin, nuclear targeted Akt doubled the proportion of DNA-synthesizing cardiomyocytes (FIG. 7D). Taken together, these results suggest that PI3K signaling is required for periostin-induced reentry of differentiated cardiomyocytes into the cell cycle and is sufficient for cell-cycle reentry in the absence of periostin.

The PI3K pathway is associated with cardiomyocyte hypertrophy and apoptosis. We tested whether periostin induces hypertrophy of differentiated cardiomyocytes. Transcription of β-myosin heavy chain (β-MHC), smooth muscle actin (SMA) and atrial natriuretic factor (ANF), markers of the fetal gene program induced in hypertrophy, was not increased by periostin in adult ventricular cardiomyocytes (RT-PCR data not shown). By contrast, positive control samples treated with phenylephrine showed increased transcription of β-MHC, SMA and ANF. Transcription of the sarco-/endoplasmic reticulum $Ca^{2+}$-ATPase (SERCA2) was slightly increased in periostin-treated samples and slightly reduced in phenylephrine-treated positive controls, consistent with decreased SERCA2 transcription in hypertrophy. These results indicate that periostin does not induce the fetal gene program.

Figure 7E:
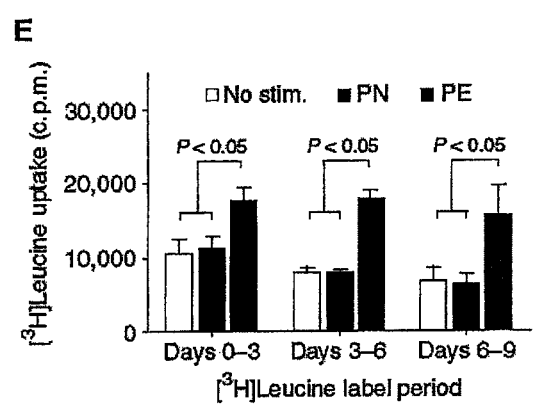
FIG. 7e is a graph showing that periostin did not induce hypertrophy, as determined by [$^3$H]-leucine uptake (n=3) (PN, periostin; PE, phenylephrine)

Induction of the fetal gene program is accompanied by increased protein synthesis leading to cardiomyocyte hypertrophy. We assessed cardiomyocyte hypertrophy by measuring uptake of [$^3$H]leucine. Whereas the positive control phenylephrine (10 mM) induced [$^3$H]leucine uptake, periostin did not induce uptake at any of the time points tested (FIG. 7E). In addition, periostin did not reduce doxorubicin or TNF-α-induced cardiomyocyte death (FIG. 2L).

VII. Recombinant Periostin and Fragments Thereof Stimulate Cardiomyocyte DNA Synthesis and Cytokinesis in vivo.

Figure 4:
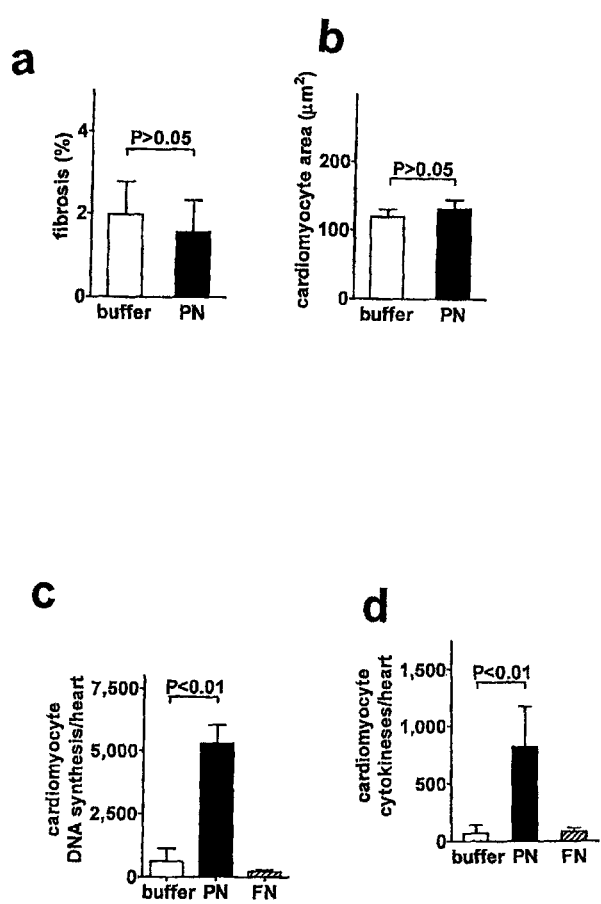
FIG. 4a is a bar graph showing digital quantification of fibrosis after buffer or periostin were injected into the myocardium of rats.
FIG. 4b is a bar graph showing cardiomyocyte cross-sectional area after buffer or periostin were injected into the myocardium of rats.
FIG. 4c is a bar graph showing quantification of cardiomyocyte DNA synthesis after buffer, periostin (PN), or fibronectin (FN) were injected into the myocardium of rats.
FIG. 4d is a bar graph showing quantification of cardiomyocyte cytokinesis after buffer, periostin (PN), or fibronectin (FN) were injected into the myocardium of rats.

To test whether periostin stimulates cardiomyocyte cell cycle re-entry in vivo, recombinant periostin was introduced into the myocardial extracellular matrix by injecting the left ventricular free wall. The presence of injected periostin was confirmed by immunofluorescence microscopy (immunofluorescence microscopy images not shown). Recombinant periostin did not induce fibrosis (FIG. 4a) or hypertrophy (FIG. 4b). Three intraperitoneal injections of BrdU with a half life of 2 hr were administered to detect a proportion of cycling cardiomyocytes. After 7 days, cycling cardiomyocytes were present near the injected areas (immunofluorescence microscopy images not shown). BrdU-positive cardiomyocytes had a differentiated phenotype as shown by striations, expression of contractile protein (troponin T), and expression of the myogenic transcription factor, MEF-2 (data not shown). Reconstruction of optical sections enabled us to assign BrU-positive nuclei unequivocally to cardiomyocytes. Periostin induced DNA synthesis in 5,322±363 cardiomyocyte nuclei per heart, an 8-fold increase compared with buffer-injected hearts (FIG. 4c). Periostin induced DNA synthesis in 0.7±0.1% and cytokinesis in 0.1±0.03% of cardiomyocyte nuclei in the injected area (FIG. 4c).

To determine if periostin stimulates cardiomyocytes to divide in vivo, we visualized the cleavage furrow during and the midbody after cytokinesis. Differentiated cardiomyocytes were detected during and after cytokinesis. Reconstruction of optical sections provided unequivocal assignment of cleavage furrow and midbody to dividing cardiomyocytes. Periostin induced cytokinesis in 821±176 cardiomyocytes per heart, an 11.5-fold increase compared with buffer-injected hearts (FIG. 4d). The proportion of cardiomyocytes visualized during cytokinesis in periostin-injected hearts was 0.008±0.002%. To confirm that cardiomyocyte proliferation is a specific effect of periostin, and not a response to nonspecific changes in the extracellular matrix, we injected hearts with fibronectin. Fibronectin did not increase cardiomyocyte DNA synthesis or cytokinesis (FIG. 4c&d). In conclusion, periostin induces DNA synthesis and division of differentiated cardiomyocytes in vivo.

To confirm that cardiomyocyte proliferation is a specific effect of periostin and not a response to nonspecific changes in the extracellular matrix, fibronectin was injected into control hearts. Fibronectin did not increase cardiomyocyte DNA synthesis or cytokinesis (FIGS. 4c & 4d). These results indicate that periostin induces DNA synthesis and division of differentiated cardiomyocytes in vivo. We determined whether mononucleated cardiomyocytes are more likely to reenter the cell-cycle in vivo by visualizing cycling cardiomyocyte nuclei with an antibody specific to phosphorylated histone H3 (H3P) on dispersed isolated cardiomyocytes. Whereas 2±0.2% of mononucleated cardiomyocytes were H3P positive, only 0.04±0.01% of binucleated cardiomyocytes were H3P positive (P=0.0005), consistent with the in vitro findings.

VIII. Periostin and Fragments Thereof Improve Cardiac Function and Reduces Fibrosis and Hypertrophy after Myocardial Infarction.

Figure 8:
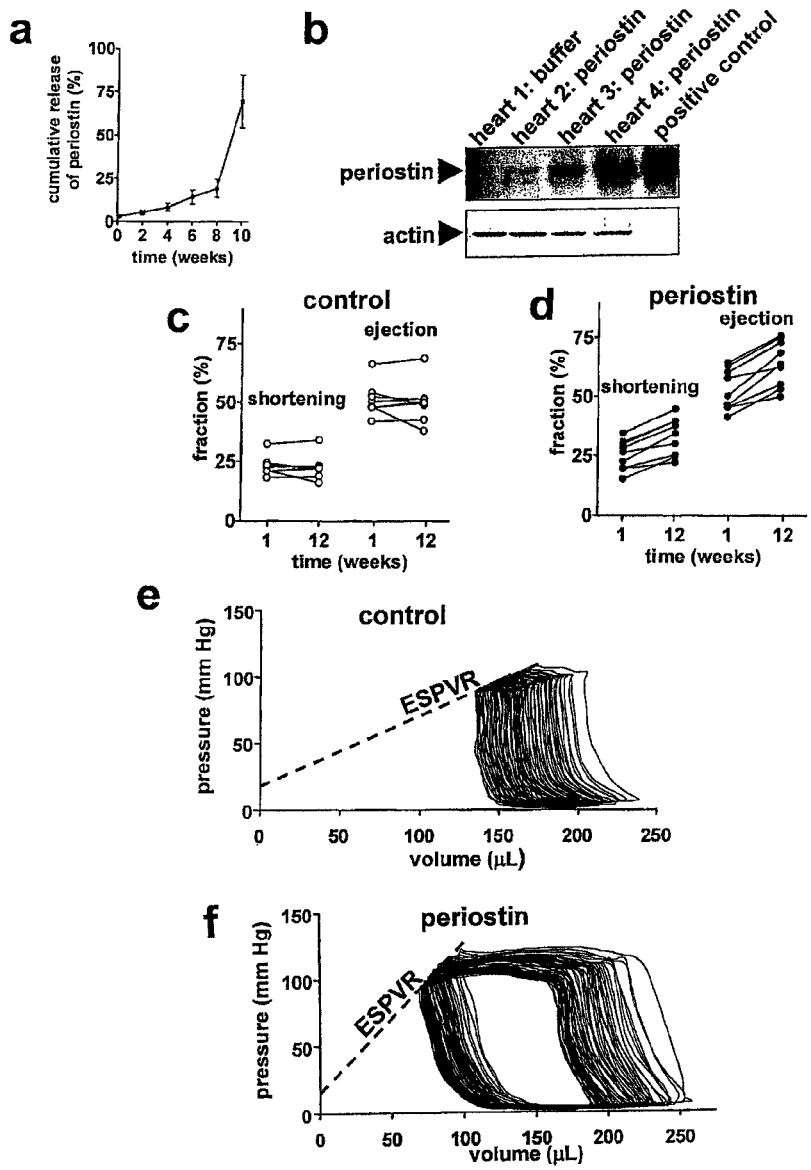
FIG. 8a shows is a graph of release kinetics of recombinant periostin from Gelfoam.
FIG. 8b is Western blot showing the presence of recombinant periostin in left ventricular free wall confirmed by immunofluorescence in 50 μg of whole heart lysate by Western blot (hearts 2-4), 5 ng of recombinant periostin loaded as positive control.
FIG. 8c is a graph of shortening and ejection fraction after 1 week and 12 weeks of administration of control buffer.
FIG. 8d is a graph of shortening and ejection fraction after 1 week and 12 weeks of administration of recombinant periostin.
FIG. 8e shows representative pressure-volume loops obtained by left-ventricular catheterization at 12 weeks after of administration of control buffer, where end-systolic pressure-volume relationship (ESPVR) is indicated by interrupted line.
FIG. 8f shows representative pressure-volume loops obtained by left-ventricular catheterization at 12 weeks after of administration of recombinant periostin, where end-systolic pressure-volume relationship (ESPVR) is indicated by interrupted line.

Sustained cardiomyocyte cell cycle activity improve function and decrease infarct size after myocardial infarction. Periostin's ability to associate with Gelfoam, a biodegradable extracellular matrix preparation is demonstrated in this Example. Thus, the invention can be used with a long-term and/or controlled release delivery system. Periostin bound to Gelfoam and was gradually released (FIG. 8a). At the time of myocardial infarction, we administered epicardial Gelfoam patches loaded with periostin or with buffer and determined the presence of recombinant periostin in the left ventricle after 12 weeks. The distance from the epicardium to the farthest diffusion range of periostin was 461±62 We confirmed presence of periostin in the left ventricle by immunoblotting (FIG. 8b). To determine if delivery of recombinant periostin improves cardiac function, echocardiography was performed 1 week and after 12 weeks after myocardial infarction (FIGS. 8c & 8d). Between 1 week and 12 weeks, the shortening fraction in periostin-treated rats increased from 25% to 33% and the ejection fraction increased from 53% to 66% (FIG. 8d & Table 3). By contrast, in control rats, the shortening and ejection fractions were unchanged.

One week after myocardial infarction, treatment and control groups had the same end-diastolic dimensions (Table 3). Importantly, at 12 weeks, the left ventricular end-diastolic dimension was significantly smaller in periostin-treated rats, suggesting improved ventricular remodeling (Table 3). We obtained a second measure of cardiac function by catheterization of the left ventricle during preload reduction (FIG. 8e&f). Treatment with periostin improved myocardial function as indicated by a steeper slope of the end-systolic pressure-volume relationship ($E_{es}$), higher preload-recruitable stroke work (PRSW), higher maximum rate of ventricular pressure rise ($dP/dt_{max}$), and a higher maximum ventricular elastance ($E_{max}$, FIG. 8e&f and Table 3). In conclusion, myocardial delivery of periostin improves ventricular remodeling and cardiac function after myocardial infarction.

TABLE 3

Periostin improves ventricular remodeling and function after myocardial infarction. Summary of echocardiography and catheterization results.

| Echocardiography | Control (n = 8) | | Periostin (n = 9) | | P between groups at 12 weeks |
|---|---|---|---|---|---|
|  | 1 week | 12 weeks | 1 week | 12 weeks |  |
| Shortening fraction (%) | 22.9 ± 1.5 | 22.6 ± 1.8 | 25.2 ± 2.1 | 33.0 ± 2.6 | 0.006 |
| P |  | 0.7 |  | <0.0001 |  |
| Ejection fraction (%) | 51.1 ± 2.5 | 50.2 ± 3.2 | 52.6 ± 2.9 | 65.9 ± 3.8 | 0.006 |
| P |  | 0.6 |  | 0.0023 |  |

TABLE 3-continued

Periostin improves ventricular remodeling and function after myocardial infarction. Summary of echocardiography and catheterization results.

| | | | | | |
|---|---|---|---|---|---|
| End-diastolic dimension (mm) | 8.1 ± 0.6 | 10.3 ± 0.4 | 8.1 ± 0.4 | 8.4 ± 0.2 | 0.02 |
| P | | 0.0086 | | 0.07 | |
| End-systolic dimension (mm) | 6.4 ± 0.4 | 7 ± 0.6 | 6.1 ± 0.4 | 6 ± 0.5 | >0.05 |
| P | | 0.2 | | 0.9 | |

| | Control (n = 8) | | Periostin (n = 7) | | |
|---|---|---|---|---|---|
| Catheterization | 1 week | 12 weeks | 1 week | 12 weeks | |
| Slope of end-systolic pressure-volume relationship (mm Hg/μL) | ND | 0.5 ± 0.01 | ND | 1.4 ± 0.2 | 0.003 |
| Preload-recruitable stroke work (mm Hg) | ND | 13.9 ± 5 | ND | 68.6 ± 13.9 | 0.02 |
| Maximum rate of left ventricular pressure rise (mm Hg/s) | ND | 3225 ± 170 | ND | 4821 ± 513 | 0.01 |
| Maximum left ventricular elastance | ND | 0.6 ± 0.01 | ND | 2.5 ± 1 | <0.05 |

Means were compared by ANOVA.

Figure 9:
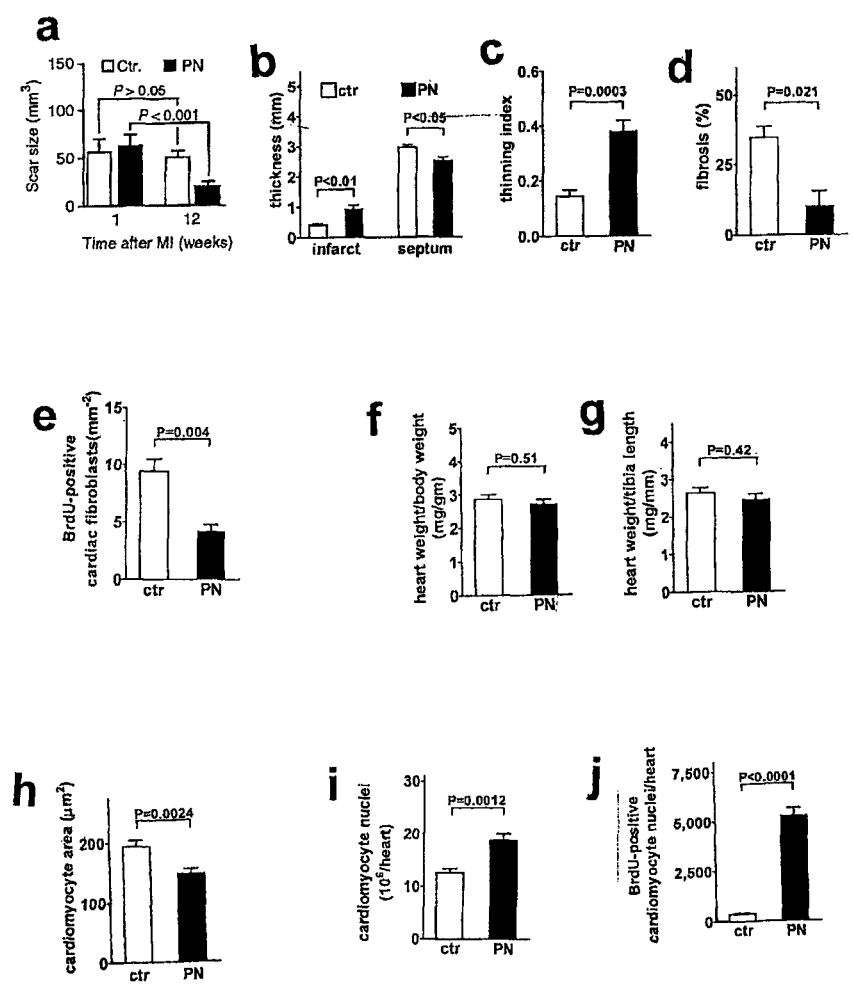
FIG. 9a is a graph of infact scar size after rats with experimental myocardial infarction (MI) were treated with control Gelfoam (ctr.) or periostin Gelfoam (PN) and analyzed after one and twelve weeks.
FIG. 9b is a graph of septal thickness after rats with experimental myocardial infarction (MI) were treated with control Gelfoam (ctr.) or periostin Gelfoam (PN) and analyzed after twelve weeks.
FIG. 9c is a graph of thinning index after rats with experimental myocardial infarction (MI) were treated with control Gelfoam (ctr.) or periostin Gelfoam (PN) and analyzed after twelve weeks.
FIG. 9d is a graph of digital determination of fibrotic area after rats with experimental myocardial infarction (MI) were treated with control Gelfoam (ctr.) or periostin Gelfoam (PN) and analyzed after twelve weeks.
FIG. 9e is a graph showing proliferating cardiac fibroblasts after rats with experimental myocardial infarction (MI) were treated with control Gelfoam (ctr.) or periostin Gelfoam (PN) and analyzed after one week.
FIG. 9f is a graph showing quantification of hypertrophy parameters heart/body weight after rats with experimental myocardial infarction (MI) were treated with control Gelfoam (ctr.) or periostin Gelfoam (PN) and analyzed after one week.
FIG. 9g is a graph showing quantification of hypertrophy parameters heart weight/tibia length ratios after rats with experimental myocardial infarction (MI) were treated with control Gelfoam (ctr.) or periostin Gelfoam (PN) and analyzed after one week.
FIG. 9h is a graph of cardiomyocyte cross-sectional area after rats with experimental myocardial infarction (MI) were treated with control Gelfoam (ctr.) or periostin Gelfoam (PN) and analyzed after one week.
FIG. 9i is a graph of the quantification of left ventricular cardiomyocyte nuclei after rats with experimental myocardial infarction (MI) were treated with control Gelfoam (ctr.) or periostin Gelfoam (PN) and analyzed after one week.
FIG. 9j is a graph of the quantification of cardiomyocyte DNA synthesis in periostin-treated heart after 3 injections with BrdU over a period of 7 days.

To determine how periostin improves cardiac function, we compared the structure of control and periostin-treated hearts at 1 and 12 weeks after myocardial infarction using histology and immunofluorescence microscopy. Periostin-treated and control hearts had the same infarct size 1 week after myocardial infarction. At 12 weeks after myocardial infarction, by contrast, periostin-treated hearts had a smaller scar volume (FIG. 9a). In periostin-treated hearts, the infarct size was 50% smaller compared with control hearts (FIG. 9a). The left ventricular free wall was thicker and the septum was thinner in periostin-treated animals (FIG. 9b). This resulted in an improved thinning index, consistent with improved remodeling (FIG. 9c). Fibrotic tissue was significantly decreased in periostin-treated hearts (FIG. 9d). Because genetic deletion of β1 and β3 integrins induces cardiac fibrosis, we tested whether application of periostin, a ligand of β1 and β3 integrins, reduces scar formation and suppresses cardiac fibroblast proliferation. The number of BrdU-positive cardiac fibroblasts was decreased in periostin-treated hearts 1 week after myocardial infarction (FIG. 9e), consistent with the decrease in fibrosis determined 12 weeks after myocardial infarction (FIG. 9d).

We analyzed ventricular remodeling by measuring the thickness of the left ventricular free wall and the interventricular septum 12 weeks after myocardial infarction. The left ventricular free wall was thicker and the septum was thinner in periostin-treated hearts (FIG. 9b), consistent with improved remodeling. We also analyzed cardiac hypertrophy, a component of ventricular remodeling. Despite the smaller infarct size in periostin-treated rats 12 weeks after myocardial infarction, heart weight was similar to that in buffer-treated rats (FIGS. 9f & 9g). By contrast, periostin-treated rats had a smaller cross-sectional cardiomyocyte area than did control rats, indicating less cellular hypertrophy (FIG. 9h). These results indicate that sustained administration of recombinant periostin reduces infarct size and improves ventricular remodeling.

To determine whether the decreased infarct size of periostin-treated hearts was related to an increased number of cardiomyocytes, we quantified cardiomyocyte nuclei. Control rats had 12.6 million left ventricular cardiomyocyte nuclei, whereas periostin-treated rats had 18.8 million left ventricular cardiomyocyte nuclei (FIG. 9i). To determine directly if periostin induces cardiomyocyte cell cycle re-entry after myocardial infarction, we quantified DNA synthesis. Differentiated cardiomyocytes, identified by expression of the cardiac contractile protein troponin I and characteristic shape, underwent DNA synthesis (not shown). Periostin induced DNA synthesis in 5,268±402 cardiomyocytes per heart, a 10-fold increase compared with buffer-treated animals (FIG. 9h). Three injections of BrdU labeled 1.4±0.5% of cardiomyocytes in the infarct border zone of periostin-treated hearts. Importantly, the rate of cardiomyocyte apoptosis was similar in control and periostin-treated hearts (data not shown). Thus, cardiomyocyte proliferation is a mechanism of increased cardiomyocyte numbers in periostin-treated hearts.

IX. Periostin Enhances Cardiac Repair

Figures 10A, 10B:
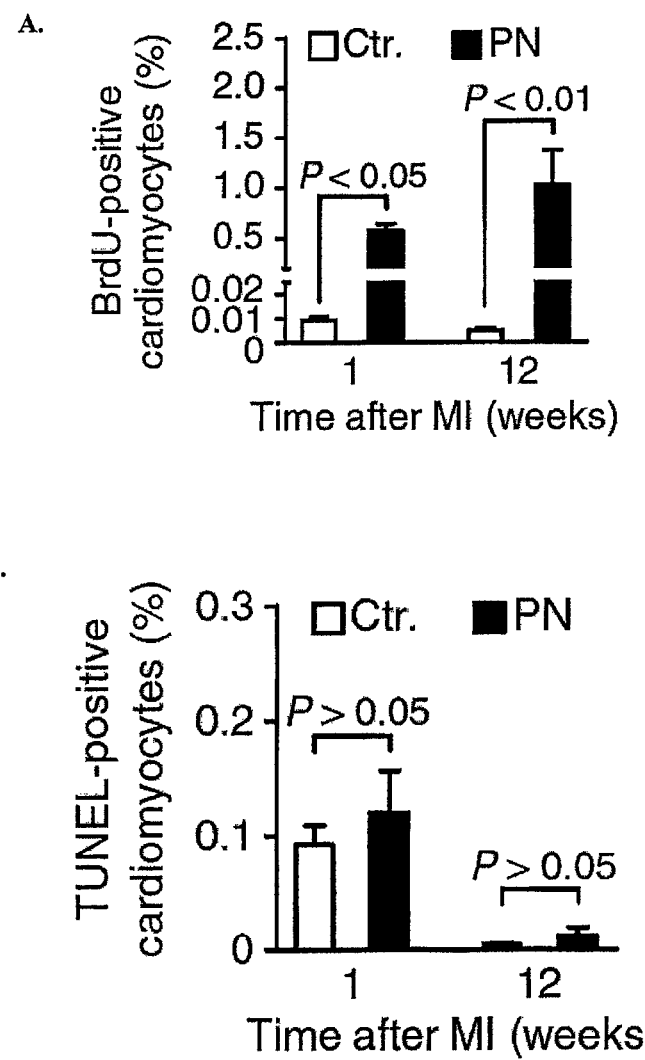
FIG. 10a is a graph of the quantification of cardiomyocyte DNA synthesis from rats with experimental myocardial infarction (MI) that were treated with control Gelfoam or periostin Gelfoam and analyzed after 1 and 12 weeks.
FIG. 10b is a graph of the quantification of apoptosis from rats with experimental myocardial infarction (MI) that were treated with control Gelfoam or periostin Gelfoam and analyzed after 1 and 12 weeks.
Figure 10C:
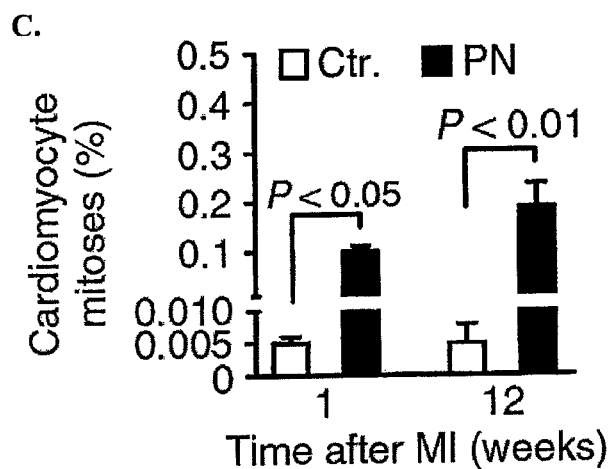
FIG. 10c is a graph of the quantification of cardiomyocyte mitoses by visualization of metaphase chromosomes from rats with experimental myocardial infarction (MI) that were treated with control Gelfoam or periostin Gelfoam and analyzed after 1 and 12 weeks.

This Example explores how periostin reduces infarct size. The in vitro results pointed to cardiomyocyte proliferation as a possible mechanism. To determine whether the decrease in infarct size correlated with cardiomyocyte cellcycle reentry, we quantified DNA synthesis in the infarct and border zone at 1 and 12 weeks after myocardial infarction. Cardiomyocytes were identified by expression of the cardiac contractile protein troponin I and by their characteristic shape (not shown). Treatment with periostin induced BrdU uptake in 0.6±0.07% of cardiomyocytes at 1 week and in 1±0.3% at 12 weeks (FIG. 10a). The proportion of apoptotic cardiomyocytes was similar in control and periostin-treated hearts at both 1 and 12 weeks (FIG. 10b). In periostin-treated hearts, however, the proportion of cycling cardiomyocytes was five-fold higher than the proportion of apoptotic cardiomyocytes at 1 week after myocardial infarction and 100-fold higher at 12 weeks (FIG. 10c), suggesting that proliferation of differentiated cardiomyocytes can be the cellular mechanism underlying the decrease in infarct size in periostin-treated hearts. We investigated this possibility by visualizing H3P in condensed metaphase chromosomes in differentiated cardiomyocytes during mitosis (not shown). Treatment with periostin induced mitosis in 0.1±0.01% of cardiomyocyte nuclei at 1 week and in 0.2±0.5% at 12 weeks (FIG. 10c).

Figure 10D:
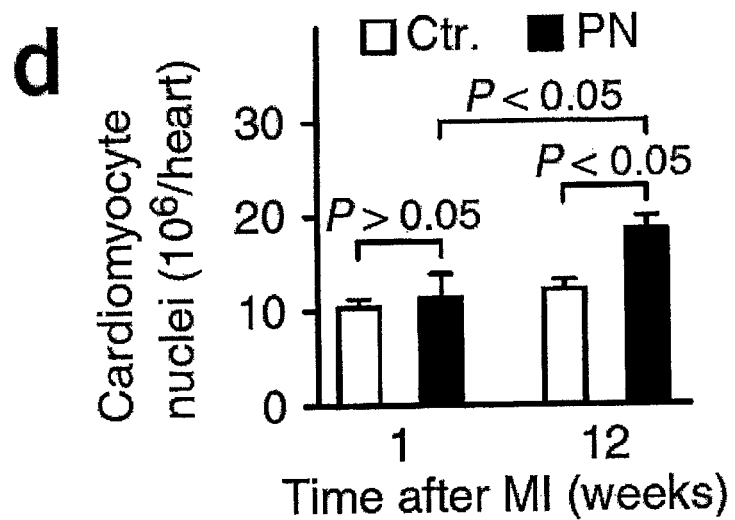
FIG. 10d is a graph of the quantification of left ventricular cardiomyocyte nuclei from rats with experimental myocardial infarction (MI) that were treated with control Gelfoam or periostin Gelfoam and analyzed after 1 and 12 weeks.

We then explored how the proliferating indices account for the observed functional improvement. After a single injection of BrdU, providing effective labeling for 6.4 h, we determined cell-cycle reentry of 23,852±1,709 differentiated cardiomyocytes per heart (n=3). The resulting rate of 3,727 cardiomyocytes entering the cell cycle per hour is calculated to result in $7.2 \times 10^6$ new cardiomyocyte nuclei per heart after 12 weeks. By quantifying cardiomyocytes with metaphase chromosomes, we independently determined 4,737±770 (n=6) cardiomyocyte mitoses in periostin-treated hearts. Chromosome condensation persisted for 1.7±0.4 h as determined by time-lapse video microscopy. This rate of cardiomyocyte mitosis is calculated to result in the generation of $5.5 \times 10^6$ cardiomyocyte nuclei over a period of 12 weeks. We also quantified cardiomyocyte nuclei directly. At 1 week after myocardial infarction, control and periostin-treated hearts had the same number of nuclei (FIG. 10d). At 12 weeks after myocardial infarction, by contrast, periostin-treated hearts had $6.2 \times 10^6$ more cardiomyocyte nuclei than did control hearts (FIG. 10d), consistent with the results based on proliferative indices. Cell-cycle reentry and division of differentiated cardiomyocytes can therefore account for the periostin-induced functional and structural improvements.

Figure 10E:
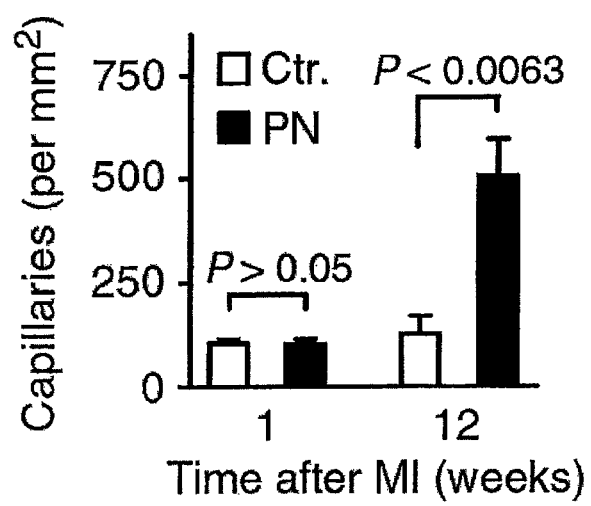
FIG. 10e is a graph of capillary density determined with antibody to von Willebrand factor (vWF) from rats with experimental myocardial infarction (MI) that were treated with control Gelfoam or periostin Gelfoam and analyzed after 1 and 12 weeks.
Figure 10:
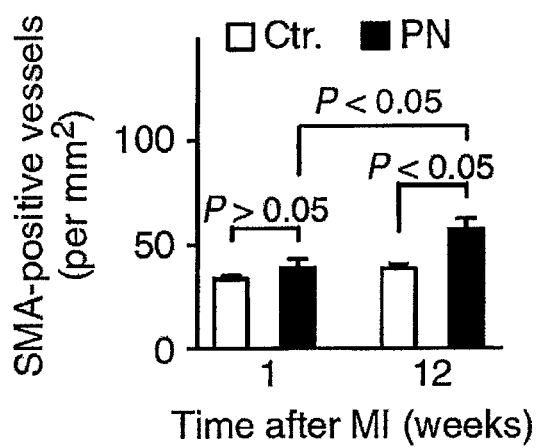
FIG. 10f is a graph of arteriolar density determined with antibody to smooth muscle actin (SMA) from rats with experimental myocardial infarction (MI) that were treated with control Gelfoam or periostin Gelfoam and analyzed after 1 and 12 weeks.
FIG. 10g is a graph of quantification of c-kit-positive stem cells in infarct area and border zone from rats with experimental myocardial infarction (MI) that were treated with control Gelfoam or periostin Gelfoam and analyzed after 1 and 12 weeks.
Figure 10G:
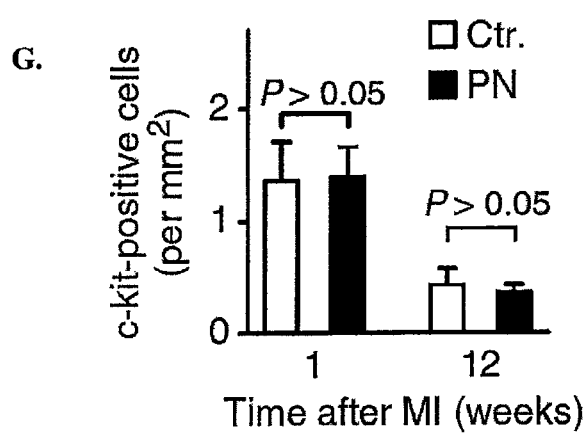

To determine whether periostin stimulates angiogenesis after myocardial infarction, we quantified the density of capillaries and arterioles in the region of the infarct and in the border zone. At 1 week, the capillary (FIG. 10e) and arteriolar (FIG. 10f) densities did not differ between control and periostin-treated hearts. At 12 weeks after myocardial infarction, however, periostin-treated hearts had a 4-fold increase in capillary and a 1.5-fold increase in arteriolar density as compared with control hearts. Improved cardiac function is associated with recruitment of c-kit-positive stem cells. However, the number of c-kit-positive cells in the infarct and border zone did not differ between periostin-treated and control hearts at 1 and at 12 weeks after myocardial infarction (FIG. 10g).

X. Periostin Stimulates Angiogenesis.

Figure 11:
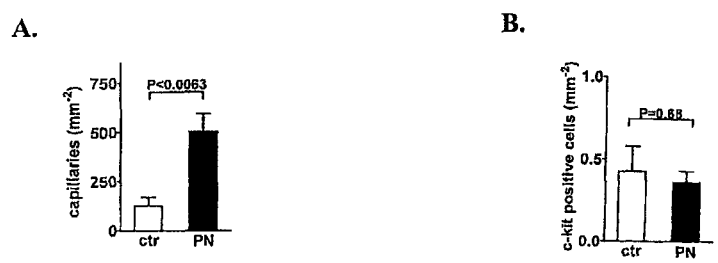
FIG. 11a is a graph of capillary density in infarcted area and border zone after rats with experimental myocardial infarction (MI) were treated with control Gelfoam (ctr.) or periostin Gelfoam (PN) and analyzed after one week.
FIG. 11b is a graph of quantification of c-kit-positive stem cells in infarcted area and border zone after rats with experimental myocardial infarction (MI) were treated with control Gelfoam (ctr.) or periostin Gelfoam (PN) and analyzed after one week.

To determine if periostin stimulates angiogenesis after myocardial infarction, we quantified the capillary density in the region of the infarct and in the border zone. Periostin-treated hearts had a 4-fold increased capillary density compared with control animals (FIG. 11A). The number of stem cells, identified with the marker c-kit (Fazel, S. et al. Cardioprotective c-kit+ cells are from the bone marrow and regulate the myocardial balance of angiogenic cytokines. *J Clin Invest* 116, 1865-77 (2006)), was similar in periostin and buffer treated hearts (FIG. 11B). In summary, periostin induces angiogenesis in the infarct area without increasing recruitment of stem cells.

The invention claimed is:

1. A method of inducing division of post mitotic mononucleated cardiomyocytes, the method comprising administering a composition comprising periostin to a subject in an amount effective to stimulate division of the post-mitotic mononucleated cardiomyocytes.

2. The method of claim 1, wherein the step of administering further comprises repairing heart tissue comprising the steps of:
   identifying a subject in need of heart tissue repair, and
   administering to the subject an effective amount of the composition, such that division of post mitotic mononucleated cardiomyocytes increases.

3. The method of claim 2, wherein the step of administering further comprises delivering the composition to a target area of the heart tissue.

4. The method of claim 3 wherein the delivering is locally to the target area.

5. The method of claim 2, wherein the administering is by parenteral administration.

6. The method of claim 2, wherein the step of administering the composition further comprises delivering the periostin composition with a slow controlled release delivery system.

7. The method of claim 2, wherein the step of administering the composition further comprises delivering the composition on a biodegradable biological scaffold.

8. The method of claim 2, wherein the administering is by intravenous administration.

9. The method of claim 2, wherein the administering is by catheter infusion.

* * * * *

SEQUENCE LISTING

```
<160> NUMBER OF SEQ ID NOS: 19

<210> SEQ ID NO 1
<211> LENGTH: 836
<212> TYPE: PRT
<213> ORGANISM: Homo sapiens

<400> SEQUENCE: 1

Met Ile Pro Phe Leu Pro Met Phe Ser Leu Leu Leu Leu Ile Val
1               5                   10                  15

Asn Pro Ile Asn Ala Asn Asn His Tyr Asp Lys Ile Leu Ala His Ser
                20                  25                  30

Arg Ile Arg Gly Arg Asp Gln Gly Pro Asn Val Cys Ala Leu Gln Gln
            35                  40                  45

Ile Leu Gly Thr Lys Lys Lys Tyr Phe Ser Thr Cys Lys Asn Trp Tyr
    50                  55                  60

Lys Lys Ser Ile Cys Gly Gln Lys Thr Thr Val Leu Tyr Glu Cys Cys
65                  70                  75                  80

Pro Gly Tyr Met Arg Met Glu Gly Met Lys Gly Cys Pro Ala Val Leu
                85                  90                  95

Pro Ile Asp His Val Tyr Gly Thr Leu Gly Ile Val Gly Ala Thr Thr
            100                 105                 110

Thr Gln Arg Tyr Ser Asp Ala Ser Lys Leu Arg Glu Glu Ile Glu Gly
        115                 120                 125

Lys Gly Ser Phe Thr Tyr Phe Ala Pro Ser Asn Glu Ala Trp Asp Asn
    130                 135                 140

Leu Asp Ser Asp Ile Arg Arg Gly Leu Glu Ser Asn Val Asn Val Glu
145                 150                 155                 160

Leu Leu Asn Ala Leu His Ser His Met Ile Asn Lys Arg Met Leu Thr
                165                 170                 175

Lys Asp Leu Lys Asn Gly Met Ile Ile Pro Ser Met Tyr Asn Asn Leu
            180                 185                 190

Gly Leu Phe Ile Asn His Tyr Pro Asn Gly Val Val Thr Val Asn Cys
```

```
                195                 200                 205
Ala Arg Ile Ile His Gly Asn Gln Ile Ala Thr Asn Gly Val Val His
210                 215                 220

Val Ile Asp Arg Val Leu Thr Gln Ile Gly Thr Ser Ile Gln Asp Phe
225                 230                 235                 240

Ile Glu Ala Glu Asp Asp Leu Ser Ser Phe Arg Ala Ala Ala Ile Thr
                245                 250                 255

Ser Asp Ile Leu Glu Ala Leu Gly Arg Asp Gly His Phe Thr Leu Phe
                260                 265                 270

Ala Pro Thr Asn Glu Ala Phe Glu Lys Leu Pro Arg Gly Val Leu Glu
                275                 280                 285

Arg Phe Met Gly Asp Lys Val Ala Ser Glu Ala Leu Met Lys Tyr His
                290                 295                 300

Ile Leu Asn Thr Leu Gln Cys Ser Glu Ser Ile Met Gly Gly Ala Val
305                 310                 315                 320

Phe Glu Thr Leu Glu Gly Asn Thr Ile Glu Ile Gly Cys Asp Gly Asp
                325                 330                 335

Ser Ile Thr Val Asn Gly Ile Lys Met Val Asn Lys Lys Asp Ile Val
                340                 345                 350

Thr Asn Asn Gly Val Ile His Leu Ile Asp Gln Val Leu Ile Pro Asp
                355                 360                 365

Ser Ala Lys Gln Val Ile Glu Leu Ala Gly Lys Gln Gln Thr Thr Phe
370                 375                 380

Thr Asp Leu Val Ala Gln Leu Gly Leu Ala Ser Ala Leu Arg Pro Asp
385                 390                 395                 400

Gly Glu Tyr Thr Leu Leu Ala Pro Val Asn Asn Ala Phe Ser Asp Asp
                405                 410                 415

Thr Leu Ser Met Val Gln Arg Leu Leu Lys Leu Ile Leu Gln Asn His
                420                 425                 430

Ile Leu Lys Val Lys Val Gly Leu Asn Glu Leu Tyr Asn Gly Gln Ile
                435                 440                 445

Leu Glu Thr Ile Gly Gly Lys Gln Leu Arg Val Phe Val Tyr Arg Thr
450                 455                 460

Ala Val Cys Ile Glu Asn Ser Cys Met Glu Lys Gly Ser Lys Gln Gly
465                 470                 475                 480

Arg Asn Gly Ala Ile His Ile Phe Arg Glu Ile Lys Pro Ala Glu
                485                 490                 495

Lys Ser Leu His Glu Lys Leu Lys Gln Asp Lys Arg Phe Ser Thr Phe
                500                 505                 510

Leu Ser Leu Leu Glu Ala Ala Asp Leu Lys Glu Leu Leu Thr Gln Pro
                515                 520                 525

Gly Asp Trp Thr Leu Phe Val Pro Thr Asn Asp Ala Phe Lys Gly Met
                530                 535                 540

Thr Ser Glu Glu Lys Glu Ile Leu Ile Arg Asp Lys Asn Ala Leu Gln
545                 550                 555                 560

Asn Ile Ile Leu Tyr His Leu Thr Pro Gly Val Phe Ile Gly Lys Gly
                565                 570                 575

Phe Glu Pro Gly Val Thr Asn Ile Leu Lys Thr Thr Gln Gly Ser Lys
                580                 585                 590

Ile Phe Leu Lys Glu Val Asn Asp Thr Leu Leu Val Asn Glu Leu Lys
                595                 600                 605

Ser Lys Glu Ser Asp Ile Met Thr Thr Asn Gly Val Ile His Val Val
                610                 615                 620
```

```
Asp Lys Leu Leu Tyr Pro Ala Asp Thr Pro Val Gly Asn Asp Gln Leu
625                 630                 635                 640

Leu Glu Ile Leu Asn Lys Leu Ile Lys Tyr Ile Gln Ile Lys Phe Val
            645                 650                 655

Arg Gly Ser Thr Phe Lys Glu Ile Pro Val Thr Val Tyr Thr Thr Lys
                660                 665                 670

Ile Ile Thr Lys Val Val Glu Pro Lys Ile Lys Val Ile Glu Gly Ser
            675                 680                 685

Leu Gln Pro Ile Ile Lys Thr Glu Gly Pro Thr Leu Thr Lys Val Lys
        690                 695                 700

Ile Glu Gly Glu Pro Glu Phe Arg Leu Ile Lys Glu Gly Glu Thr Ile
705                 710                 715                 720

Thr Glu Val Ile His Gly Glu Pro Ile Ile Lys Lys Tyr Thr Lys Ile
                725                 730                 735

Ile Asp Gly Val Pro Val Glu Ile Thr Glu Lys Glu Thr Arg Glu Glu
            740                 745                 750

Arg Ile Ile Thr Gly Pro Glu Ile Lys Tyr Thr Arg Ile Ser Thr Gly
        755                 760                 765

Gly Gly Glu Thr Glu Thr Leu Lys Lys Leu Leu Gln Glu Val
770                 775                 780

Thr Lys Val Thr Lys Phe Ile Glu Gly Gly Asp Gly His Leu Phe Glu
785                 790                 795                 800

Asp Glu Glu Ile Lys Arg Leu Leu Gln Gly Asp Thr Pro Val Arg Lys
                805                 810                 815

Leu Gln Ala Asn Lys Lys Val Gln Gly Ser Arg Arg Leu Arg Glu
            820                 825                 830

Gly Arg Ser Gln
        835

<210> SEQ ID NO 2
<211> LENGTH: 20
<212> TYPE: DNA
<213> ORGANISM: Artificial
<220> FEATURE:
<223> OTHER INFORMATION: Synthetic Construct - Primer

<400> SEQUENCE: 2
atacagtgcg gtgtccaaca                                              20

<210> SEQ ID NO 3
<211> LENGTH: 20
<212> TYPE: DNA
<213> ORGANISM: Artificial
<220> FEATURE:
<223> OTHER INFORMATION: Synthetic Construct - Primer

<400> SEQUENCE: 3
ggatcttttg cgatctgctc                                              20

<210> SEQ ID NO 4
<211> LENGTH: 21
<212> TYPE: DNA
<213> ORGANISM: Artificial
<220> FEATURE:
<223> OTHER INFORMATION: Synthetic Construct - Primer

<400> SEQUENCE: 4
ggagaagatt tggcaccaca c                                            21
```

```
<210> SEQ ID NO 5
<211> LENGTH: 21
<212> TYPE: DNA
<213> ORGANISM: Artificial
<220> FEATURE:
<223> OTHER INFORMATION: Synthetic Construct - Primer

<400> SEQUENCE: 5
cagggaggaa gaggatgcgg c                                              21

<210> SEQ ID NO 6
<211> LENGTH: 20
<212> TYPE: DNA
<213> ORGANISM: Artificial
<220> FEATURE:
<223> OTHER INFORMATION: Synthetic Construct - Primer

<400> SEQUENCE: 6
cttcaaccac cacatgttcg                                                20

<210> SEQ ID NO 7
<211> LENGTH: 20
<212> TYPE: DNA
<213> ORGANISM: Artificial
<220> FEATURE:
<223> OTHER INFORMATION: Synthetic Construct - Primer

<400> SEQUENCE: 7
tacaggtgca tcagctccag                                                20

<210> SEQ ID NO 8
<211> LENGTH: 20
<212> TYPE: DNA
<213> ORGANISM: Artificial
<220> FEATURE:
<223> OTHER INFORMATION: Synthetic Construct - Primer

<400> SEQUENCE: 8
gtcggtatgg gtcagaagga                                                20

<210> SEQ ID NO 9
<211> LENGTH: 20
<212> TYPE: DNA
<213> ORGANISM: Artificial
<220> FEATURE:
<223> OTHER INFORMATION: Synthetic Construct - Primer

<400> SEQUENCE: 9
cttttccagg gaggaggaag                                                20

<210> SEQ ID NO 10
<211> LENGTH: 20
<212> TYPE: DNA
<213> ORGANISM: Artificial
<220> FEATURE:
<223> OTHER INFORMATION: Synthetic Construct - Primer

<400> SEQUENCE: 10
actggtgatg gtgtgaacga                                                20

<210> SEQ ID NO 11
<211> LENGTH: 20
<212> TYPE: DNA
<213> ORGANISM: Artificial
<220> FEATURE:
<223> OTHER INFORMATION: Synthetic Construct - Primer
```

-continued

<400> SEQUENCE: 11
tacggggact caaagattgc                                              20

<210> SEQ ID NO 12
<211> LENGTH: 20
<212> TYPE: DNA
<213> ORGANISM: Artificial
<220> FEATURE:
<223> OTHER INFORMATION: Synthetic Construct - Primer

<400> SEQUENCE: 12
ctcatgacca cagtccatgc                                              20

<210> SEQ ID NO 13
<211> LENGTH: 20
<212> TYPE: DNA
<213> ORGANISM: Artificial
<220> FEATURE:
<223> OTHER INFORMATION: Synthetic Construct - Primer

<400> SEQUENCE: 13
atgtaggcca tgaggtccac                                              20

<210> SEQ ID NO 14
<211> LENGTH: 64
<212> TYPE: DNA
<213> ORGANISM: Artificial
<220> FEATURE:
<223> OTHER INFORMATION: Synthetic Construct

<400> SEQUENCE: 14
tgctgttagc ttgacacctg cgtcttgttt tggccactga ctgacaagac gcatgtcaag   60
ctaa                                                               64

<210> SEQ ID NO 15
<211> LENGTH: 64
<212> TYPE: DNA
<213> ORGANISM: Artificial
<220> FEATURE:
<223> OTHER INFORMATION: Synthetic Construct - Primer

<400> SEQUENCE: 15
tgctgttgag ttccagcctt catcgggttt tggccactga ctgacccgat gaactggaac   60
tcaa                                                               64

<210> SEQ ID NO 16
<211> LENGTH: 64
<212> TYPE: DNA
<213> ORGANISM: Artificial
<220> FEATURE:
<223> OTHER INFORMATION: Synthetic Construct - Primer

<400> SEQUENCE: 16
tgctgttgcc ttgctgaatg aacttggttt tggccactga ctgaccaagt tcacagcaag   60
gcaa                                                               64

<210> SEQ ID NO 17
<211> LENGTH: 64
<212> TYPE: DNA
<213> ORGANISM: Artificial
<220> FEATURE:
<223> OTHER INFORMATION: Synthetic Construct - Primer

```
<400> SEQUENCE: 17
tgctgattcc ttgtaaacag gctggagttt tggccactga ctgactccag cctttacaag    60
gaat                                                                 64

<210> SEQ ID NO 18
<211> LENGTH: 64
<212> TYPE: DNA
<213> ORGANISM: Artificial
<220> FEATURE:
<223> OTHER INFORMATION: Synthetic Construct - Primer

<400> SEQUENCE: 18
tgctgtttcc agacagtgtg cccactgttt tggccactga ctgacagtgg gcactgtctg    60
gaaa                                                                 64

<210> SEQ ID NO 19
<211> LENGTH: 64
<212> TYPE: DNA
<213> ORGANISM: Artificial
<220> FEATURE:
<223> OTHER INFORMATION: Synthetic Construct - Primer

<400> SEQUENCE: 19
tgctgtgaag gaccacctct acttctgttt tggccactga ctgacagaag taggtggtcc    60
ttca                                                                 64
```